(12) United States Patent
Zeng

(10) Patent No.: US 7,943,729 B2
(45) Date of Patent: May 17, 2011

(54) DOMINANT B CELL EPITOPES AND METHODS OF MAKING AND USING THEREOF

(75) Inventor: Gang Zeng, Los Angeles, CA (US)

(73) Assignees: The Regents of the University of California, Oakland, CA (US); National Institutes of Health, Rockville, MD (US)

( * ) Notice: Subject to any disclaimer, the term of this patent is extended or adjusted under 35 U.S.C. 154(b) by 239 days.

(21) Appl. No.: 12/182,652

(22) Filed: Jul. 30, 2008

(65) Prior Publication Data

US 2010/0136527 A1    Jun. 3, 2010

Related U.S. Application Data

(62) Division of application No. 11/569,250, filed as application No. PCT/US2005/017589 on May 19, 2005, now Pat. No. 7,420,032.

(60) Provisional application No. 60/572,474, filed on May 20, 2004.

(51) Int. Cl.
  *A61K 38/00* (2006.01)
  *G01N 33/53* (2006.01)

(52) U.S. Cl. ........................................ 530/300; 435/7.1

(58) Field of Classification Search .................. 530/300; 435/7.1

See application file for complete search history.

(56) References Cited

U.S. PATENT DOCUMENTS

| | | | |
|---|---|---|---|
| 6,251,603 B1 | 6/2001 | Jager et al. | 435/6 |
| 6,338,947 B1 | 1/2002 | Sahin et al. | 435/7.1 |
| 6,504,010 B1 * | 1/2003 | Wang et al. | 530/350 |
| 6,525,177 B2 | 2/2003 | Stockert et al. | 530/350 |
| 2002/0193295 A1 | 12/2002 | Calenoff | |
| 2003/0003516 A1 | 1/2003 | Robinson | |
| 2003/0170255 A1 * | 9/2003 | Watanabe et al. | 424/185.1 |
| 2005/0070028 A1 | 3/2005 | Ito | |
| 2005/0261166 A1 | 11/2005 | Wang et al. | 514/2 |

OTHER PUBLICATIONS

Stratagene Catalog, 1988, p. 39.*

* cited by examiner

*Primary Examiner* — Hong Sang
(74) *Attorney, Agent, or Firm* — Suzannah K. Sundby, Esq.; Smith, Gambrell & Russell, LLP

(57) ABSTRACT

Disclosed are methods for obtaining at least one epitope suitable for detecting the presence of an antibody against a tumor associated antigen of a cancer in a sample. Kits, assays, and substrates employing the epitopes of the present invention are disclosed. Also disclosed are epitopes of NY-ESO-1 and XAGE-1b and methods of using thereof.

11 Claims, 11 Drawing Sheets

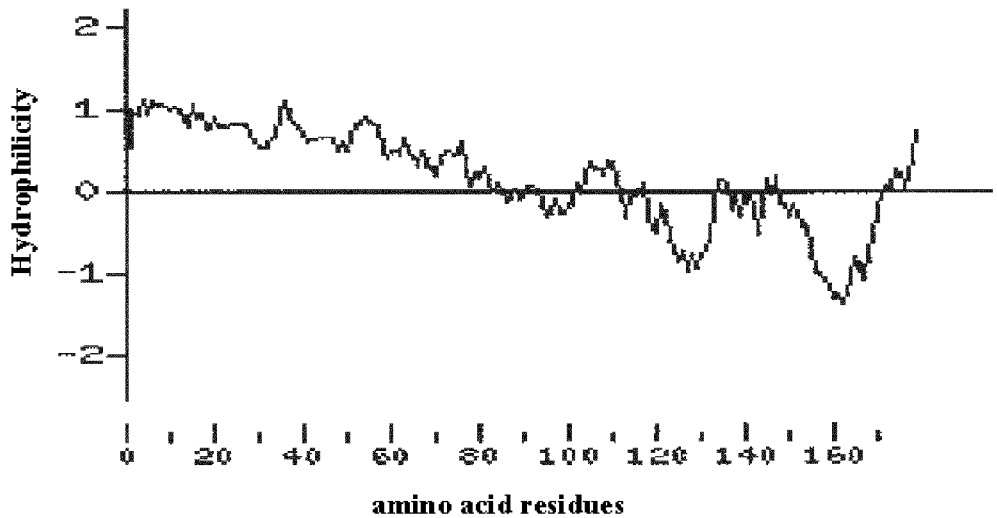

Figure 1A

```
MQAEGRGTGGSTGDADGPGGPGIPDGPGGNAGGPGEAGATGGRGPRGAGAARASGPGGGA
CCCCCCCCCCCCCCCCCCCCCCCCCCCCCCCCCCCCCCCCCCCCCCCCCEECCCCCCCC
............S.TTSTT......STT.....TT..T.......TT.HHEE..STTS..

PRGPHGGAASGLNGCCRCGARGPESRLLEFYLAMPFATPMEAELARRSLAQDAPPLPVPG
CCCCCCCCCCCCCCCCCCCCCCCCCHHHHHHHHCCCCCHHHHHHHHHHCCCCCCCCCCC
....T..HETT.TT..ETT..SHHHHHHHHHH..T..HHHHHHHHHHHT.......E

VLLKEFTVSGNILTIRLTAADHRQLQLSISSCLQQLSLLMWITQCFLPVFLAQPPSGQRR
EEEEEEEECCCEEEEEEECHHHHHHHHHHHHHHHHHHHHHHHHHHHCHHHECCCCCCCC
EEEEEEEEESHEEEEEEHHHHHHHHHHHHHHHHHHHHHHHHHHHHHHHEHE...TT...
```

Figure 1B

SEQUENCE LISTING

```
<160> NUMBER OF SEQ ID NOS: 17

<210> SEQ ID NO 1
<211> LENGTH: 180
<212> TYPE: PRT
<213> ORGANISM: Homo sapiens

<400> SEQUENCE: 1

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 2
<211> LENGTH: 50
<212> TYPE: PRT
<213> ORGANISM: Homo sapiens

<400> SEQUENCE: 2

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala
    50
```

```
<210> SEQ ID NO 3
<211> LENGTH: 20
<212> TYPE: PRT
<213> ORGANISM: Homo sapiens

<400> SEQUENCE: 3

Ser Thr Gly Asp Ala Asp Gly Pro Gly Gly Pro Gly Ile Pro Asp Gly
1               5                   10                  15

Pro Gly Gly Asn
            20

<210> SEQ ID NO 4
<211> LENGTH: 40
<212> TYPE: PRT
<213> ORGANISM: Homo sapiens

<400> SEQUENCE: 4

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr
        35                  40

<210> SEQ ID NO 5
<211> LENGTH: 20
<212> TYPE: PRT
<213> ORGANISM: Homo sapiens

<400> SEQUENCE: 5

Met Gln Ala Glu Gly Arg Gly Thr Gly Gly Ser Thr Gly Asp Ala Asp
1               5                   10                  15

Gly Pro Gly Gly
            20

<210> SEQ ID NO 6
<211> LENGTH: 20
<212> TYPE: PRT
<213> ORGANISM: Homo sapiens

<400> SEQUENCE: 6

Arg Gly Thr Gly Gly Ser Thr Gly Asp Ala Asp Gly Pro Gly Gly Pro
1               5                   10                  15

Gly Ile Pro Asp
            20

<210> SEQ ID NO 7
<211> LENGTH: 20
<212> TYPE: PRT
<213> ORGANISM: Homo sapiens

<400> SEQUENCE: 7

Asp Gly Pro Gly Gly Pro Gly Ile Pro Asp Gly Pro Gly Gly Asn Ala
1               5                   10                  15

Gly Gly Pro Gly
            20

<210> SEQ ID NO 8
<211> LENGTH: 20
<212> TYPE: PRT
<213> ORGANISM: Homo sapiens
```

-continued

```
<400> SEQUENCE: 8

Pro Gly Ile Pro Asp Gly Pro Gly Gly Asn Ala Gly Gly Pro Gly Glu
1               5                   10                  15

Ala Gly Ala Thr
            20

<210> SEQ ID NO 9
<211> LENGTH: 20
<212> TYPE: PRT
<213> ORGANISM: Homo sapiens

<400> SEQUENCE: 9

Gly Pro Gly Gly Asn Ala Gly Gly Pro Gly Glu Ala Gly Ala Thr Gly
1               5                   10                  15

Gly Arg Gly Pro
            20

<210> SEQ ID NO 10
<211> LENGTH: 20
<212> TYPE: PRT
<213> ORGANISM: Homo sapiens

<400> SEQUENCE: 10

Ala Gly Gly Pro Gly Glu Ala Gly Ala Thr Gly Gly Arg Gly Pro Arg
1               5                   10                  15

Gly Ala Gly Ala
            20

<210> SEQ ID NO 11
<211> LENGTH: 23
<212> TYPE: DNA
<213> ORGANISM: Artificial Sequence
<220> FEATURE:
<223> OTHER INFORMATION: Primer for human ESO1-F.

<400> SEQUENCE: 11
cagggctgaa tggatgctgc aga                                         23

<210> SEQ ID NO 12
<211> LENGTH: 21
<212> TYPE: DNA
<213> ORGANISM: Artificial Sequence
<220> FEATURE:
<223> OTHER INFORMATION: Primer for human ESO1-R.

<400> SEQUENCE: 12
gcgcctctgc cctgagggag g                                           21

<210> SEQ ID NO 13
<211> LENGTH: 23
<212> TYPE: DNA
<213> ORGANISM: Artificial Sequence
<220> FEATURE:
<223> OTHER INFORMATION: Primer for human LAGE1-F.

<400> SEQUENCE: 13
ctgcgcagga tggaaggtgc ccc                                         23

<210> SEQ ID NO 14
<211> LENGTH: 21
<212> TYPE: DNA
<213> ORGANISM: Artificial Sequence
<220> FEATURE:
<223> OTHER INFORMATION: Primer for human LAGE1-R.
```

-continued

```
<400> SEQUENCE: 14
gcgcctctgc cctgagggag c                                              21

<210> SEQ ID NO 15
<211> LENGTH: 81
<212> TYPE: PRT
<213> ORGANISM: Homo sapiens

<400> SEQUENCE: 15

Met Glu Ser Pro Lys Lys Asn Gln Gln Leu Lys Val Gly Ile Leu
1               5                   10                  15

His Leu Gly Ser Arg Gln Lys Lys Ile Arg Ile Gln Leu Arg Ser Gln
            20                  25                  30

Cys Ala Thr Trp Lys Val Ile Cys Lys Ser Cys Ile Ser Gln Thr Pro
        35                  40                  45

Gly Ile Asn Leu Asp Leu Gly Ser Gly Val Lys Val Lys Ile Ile Pro
    50                  55                  60

Lys Glu Glu His Cys Lys Met Pro Glu Ala Gly Glu Glu Gln Pro Gln
65                  70                  75                  80

Val

<210> SEQ ID NO 16
<211> LENGTH: 25
<212> TYPE: PRT
<213> ORGANISM: Homo sapiens

<400> SEQUENCE: 16

Met Glu Ser Pro Lys Lys Asn Gln Gln Leu Lys Val Gly Ile Leu
1               5                   10                  15

His Leu Gly Ser Arg Gln Lys Lys Ile
            20                  25

<210> SEQ ID NO 17
<211> LENGTH: 25
<212> TYPE: PRT
<213> ORGANISM: Homo sapiens

<400> SEQUENCE: 17

Gly Val Lys Val Lys Ile Ile Pro Lys Glu Glu His Cys Lys Met Pro
1               5                   10                  15

Glu Ala Gly Glu Glu Gln Pro Gln Val
            20                  25
```

DOMINANT B CELL EPITOPES AND METHODS OF MAKING AND USING THEREOF

CROSS-REFERENCE TO RELATED APPLICATIONS

This application is a divisional of U.S. patent application Ser. No. 11/569,250, filed 17 Nov. 2006, now U.S. Pat. No. 7,420,032, which is a 371 of PCT/US2005/017589, filed 19 May 2005, which claims the benefit of U.S. Provisional Serial Application No. 60/572,474, filed 20 May 2004, all of which are herein incorporated by reference in their entirety.

STATEMENT REGARDING GOVERNMENT SPONSORED RESEARCH OR DEVELOPMENT

This invention was made with Government support of Grant No. 1 P50 CA92131 and 1 P50 CA90388, awarded by the National Cancer Institute. The Government has certain rights in this invention.

This research is supported in part by the UCLA prostate cancer SPORE developmental project award (1 P50 CA92131) and the UCLA lung cancer SPORE career development (1 P50 CA90388).

BACKGROUND OF THE INVENTION

1. Field of the Invention

The present invention generally relates to tumor associated antigens. In particular, the present invention generally relates to dominant B cell epitopes of tumor associated antigens and methods of making and using thereof.

2. Description of the Related Art

In the last 10 years, molecular identification of tumor associated antigens (TAA) has clearly demonstrated that the human immune system can react with endogenously arising cancer cells. See Van der Bruggen, P, et al. (1991) Science 254(5038):1643-1647. Both the cellular and humoral arms of the human immune system recognize autologous TAA derived from cancer cells. See Rosenberg, S A (2001) Nature 411(6835):380-384; and Old, L J, and Chen, Y T (1998) J Exp Med 187(8):1163-1167. Of particular interest to the serological analysis of human cancers is the identification of TAA recognized by antibodies (Ab) present in the sera of cancer subjects. See Sahin, U, et al. (1997) Curr Opin Immunol 9(5):709-716. SEREX, or the serological analysis of recombinant cDNA expression libraries of human cancers, has been the primary approach to identify TAA based on their recognition by Ab.

Up to now, there are many TAA identified based on recognition by Ab present in subjects' sera. See Scanlan, M J, et al. (2002) Immunol Rev 188(1):22-32. These TAA include targets from many cancer types, such as melanoma, renal cancer, Hodgkin's disease, esophageal cancer, lung cancer, colon cancer, gastric cancer, breast cancer, prostate cancer and so on. The discovery of these TAA provides molecular details of the humoral immune response to autologous tumors. More importantly, the discovery of these molecules awakens the old hope of finding serological markers for cancer detection, diagnosis, and prognosis. However, most of the SEREX-defined antigens do not or only react with few allogeneic sera. Unfortunately, investigating Ab responses against a large panel of TAA that covers a wide spectrum of subjects with a particular cancer requires the purification of individual TAA protein, which is expensive and difficult to achieve. Therefore, a need exists for epitopes from TAA for the detection of Ab against TAA.

SUMMARY OF THE INVENTION

The present invention generally provides epitopes from tumor associated antigens for the detection of antibodies against TAAs.

In some embodiments, the present invention provides a method for obtaining at least one epitope suitable for detecting the presence of at least one antibody against a tumor associated antigen of a cancer which comprises selecting at least one tumor associated antigen known to be expressed by the cancer, predicting the hydrophilicity and surface accessibility of a plurality of peptides having about 9 to about 12 consecutive amino acid residues of the tumor associated antigen, screening the peptides having a desired hydrophilicity and surface accessibility against antibodies that specifically bind the tumor associated antigen, and detecting the peptides which specifically bind the antibodies. In some embodiments, the cancer is melanoma, prostate cancer, non-small cell lung cancer, esophageal cancer, gastric cancer, hepatocellular carcinoma, bladder cancer, ovarian cancer, breast cancer, testicular cancer, prostate cancer, myeloma, small cell lung cancer or sarcoma. In some embodiments, the tumor associated antigen is NY-ESO-1 or XAGE-1b. In some embodiments, the epitope has a sequence of about 9 or more, preferably about 12 or more, consecutive amino acid residues of the tumor associated antigen. In some embodiments, the epitope (a) comprises at least 20 consecutive amino acid residues of SEQ ID NO:2; (b) consists essentially of at least 20 consecutive amino acid residues of SEQ ID NO:2; (c) consists of at least 20 consecutive amino acid residues of SEQ ID NO:2; (d) consists essentially of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (e) consists of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (f) comprises at least 20 consecutive amino acid residues of SEQ ID NO:15; (g) consists essentially of at least 20 consecutive amino acid residues of SEQ ID NO:15; (h) consists of at least 20 consecutive amino acid residues of SEQ ID NO:15; (i) consists essentially of SEQ ID NO:16 or SEQ ID NO:17; or (j) consists of SEQ ID NO:16 or SEQ ID NO:17.

In some embodiments, the present invention provides epitopes made by selecting at least one tumor associated antigen known to be expressed by a cancer, predicting the hydrophilicity and surface accessibility of a plurality of peptides having about 9 to about 12 consecutive amino acid residues of a tumor associated antigen expressed by the cancer, screening the peptides having a desired hydrophilicity and surface accessibility against antibodies that specifically bind the tumor associated antigen, and detecting the peptides which specifically bind the antibodies. In some embodiments, the cancer is melanoma, prostate cancer, non-small cell lung cancer, esophageal cancer, gastric cancer, hepatocellular carcinoma, bladder cancer, ovarian cancer, breast cancer, testicular cancer, prostate cancer, myeloma, small cell lung cancer or sarcoma. In some embodiments, the tumor associated antigen is NY-ESO-1 or XAGE-1b. In some embodiments, the epitope has a sequence of about 9 or more, preferably about 12 or more, consecutive amino acid residues of the tumor associated antigen. In some embodiments, the epitope (a) comprises at least 20 consecutive amino acid residues of SEQ ID NO:2; (b) consists essentially of at least 20 consecutive amino acid residues of SEQ ID NO:2; (c) consists of at least 20 consecutive amino acid residues of SEQ ID NO:2; (d) consists essentially of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (e) consists of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (0 comprises at least 20 consecutive amino acid residues of SEQ ID NO:15; (g) consists essentially of at least 20 consecutive amino acid residues of SEQ ID NO:15; (h) consists of at least 20 consecutive amino acid residues of SEQ ID NO:15; (i) consists essentially of SEQ ID NO:16 or SEQ ID NO:17; or (j) consists of SEQ ID NO:16 or SEQ ID NO:17.

In some embodiments, the present invention provides a substrate which comprises at least one epitope of the present invention immobilized thereon. The substrate may be made from a variety of materials including silicon, silica, quartz, glass, controlled pore glass, carbon, alumina, titania, tantalum oxide, germanium, silicon nitride, zeolites, gallium arsenide, gold, platinum, aluminum, copper and titanium, polymers, combinations thereof, and the like. The substrates upon which are preferably made of materials that are optically transparent. The substrates are preferably made of materials that do not substantially affect any assay and reagents in which the substrates of the present invention are employed. In preferred embodiments, the substrates comprise polymers such as polystyrene; poly(tetra)fluoroethylene (PTFE); poly-vinylidenedifluoride; polycarbonate (PC); polymethylmethacrylate (PMMA); polyvinylethylene; polyethyleneimine; poly(etherether)ketone; polyoxymethylene (POM); polyvinylphenol; polylactides; polymethacrylimide (PMI); polyetherimide (PEI), cyclo-olefin, polyalkenesulfone (PAS); polypropylene; polyethylene; polyhydroxyethylmethacrylate (HEMA); polydimethylsiloxane (PDMS); polyacrylamide; polyimide; and block-copolymers, and the like, and combinations thereof.

In some embodiments, the present invention provides a kit comprising at least one epitope of the present invention packaged together with at least one reagent, such those used in immunoassays. In some embodiments, the epitope is made by selecting at least one tumor associated antigen known to be expressed by a cancer, predicting the hydrophilicity and surface accessibility of a plurality of peptides having about 9 to about 12 consecutive amino acid residues of a tumor associated antigen expressed by the cancer, screening the peptides having a desired hydrophilicity and surface accessibility against antibodies that specifically bind the tumor associated antigen, and detecting the peptides which specifically bind the antibodies. In some embodiments, the cancer is melanoma, prostate cancer, non-small cell lung cancer, esophageal cancer, gastric cancer, hepatocellular carcinoma, bladder cancer, ovarian cancer, breast cancer, testicular cancer, prostate cancer, myeloma, small cell lung cancer or sarcoma. In some embodiments, the tumor associated antigen is NY-ESO-1 or XAGE-1b. In some embodiments, the epitope has a sequence of about 9 or more, preferably about 12 or more, consecutive amino acid residues of the tumor associated antigen. In some embodiments, the epitope (a) comprises at least 20 consecutive amino acid residues of SEQ ID NO:2; (b) consists essentially of at least 20 consecutive amino acid residues of SEQ ID NO:2; (c) consists of at least 20 consecutive amino acid residues of SEQ ID NO:2; (d) consists essentially of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (e) consists of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (f) comprises at least 20 consecutive amino acid residues of SEQ ID NO:15; (g) consists essentially of at least 20 consecutive amino acid residues of SEQ ID NO:15; (h) consists of at least 20 consecutive amino acid residues of SEQ ID NO:15; (i) consists essentially of SEQ ID NO:16 or SEQ ID NO:17; or (j) consists of SEQ ID NO:16 or SEQ ID NO:17.

In some embodiments, the present invention provides a complex comprising at least one epitope of the present invention and an antibody which selectively binds the epitope. In some embodiments, the epitope is made by selecting at least one tumor associated antigen known to be expressed by a cancer, predicting the hydrophilicity and surface accessibility of a plurality of peptides having about 9 to about 12 consecutive amino acid residues of a tumor associated antigen expressed by the cancer, screening the peptides having a desired hydrophilicity and surface accessibility against antibodies that specifically bind the tumor associated antigen, and detecting the peptides which specifically bind the antibodies. In some embodiments, the cancer is melanoma, prostate cancer, non-small cell lung cancer, esophageal cancer, gastric cancer, hepatocellular carcinoma, bladder cancer, ovarian cancer, breast cancer, testicular cancer, prostate cancer, myeloma, small cell lung cancer or sarcoma. In some embodiments, the tumor associated antigen is NY-ESO-1 or XAGE-1b. In some embodiments, the epitope has a sequence of about 9 or more, preferably about 12 or more, consecutive amino acid residues of the tumor associated antigen. In some embodiments, the epitope (a) comprises at least 20 consecutive amino acid residues of SEQ ID NO:2; (b) consists essentially of at least 20 consecutive amino acid residues of SEQ ID NO:2; (c) consists of at least 20 consecutive amino acid residues of SEQ ID NO:2; (d) consists essentially of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (e) consists of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (f) comprises at least 20 consecutive amino acid residues of SEQ ID NO:15; (g) consists essentially of at least 20 consecutive amino acid residues of SEQ ID NO:15; (h) consists of at least 20 consecutive amino acid residues of SEQ ID NO:15; (i) consists essentially of SEQ ID NO:16 or SEQ ID NO:17; or (j) consists of SEQ ID NO:16 or SEQ ID NO:17.

In some embodiments, the present invention provides a method for assaying, enriching, isolating or purifying at least one antibody against a tumor associated antigen or a B cell secreting the antibody which comprises contacting the antibody with an epitope of the present invention. In some embodiments, the epitope is made by selecting at least one tumor associated antigen known to be expressed by a cancer, predicting the hydrophilicity and surface accessibility of a plurality of peptides having about 9 to about 12 consecutive amino acid residues of a tumor associated antigen expressed by the cancer, screening the peptides having a desired hydrophilicity and surface accessibility against antibodies that specifically bind the tumor associated antigen, and detecting the peptides which specifically bind the antibodies. In some embodiments, the cancer is melanoma, prostate cancer, non-small cell lung cancer, esophageal cancer, gastric cancer, hepatocellular carcinoma, bladder cancer, ovarian cancer, breast cancer, testicular cancer, prostate cancer, myeloma, small cell lung cancer or sarcoma. In some embodiments, the tumor associated antigen is NY-ESO-1 or XAGE-1b. In some embodiments, the epitope has a sequence of about 9 or more, preferably about 12 or more, consecutive amino acid residues of the tumor associated antigen. In some embodiments, the epitope (a) comprises at least 20 consecutive amino acid residues of SEQ ID NO:2; (b) consists essentially of at least 20 consecutive amino acid residues of SEQ ID NO:2; (c) consists of at least 20 consecutive amino acid residues of SEQ ID NO:2; (d) consists essentially of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (e) consists of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (f) comprises at least 20 consecutive amino acid residues of SEQ ID NO:15; (g) consists essentially of at least 20 consecutive amino acid residues of SEQ ID NO:15; (h) consists of at least 20 consecutive amino acid residues of SEQ ID NO:15; (i) consists essentially of SEQ ID NO:16 or SEQ ID NO:17; or (j) consists of SEQ ID NO:16 or SEQ ID NO:17.

In some embodiments the present invention provides an assay which comprises contacting at least one epitope of the present invention with a sample and detecting whether an antibody in the sample selectively binds the epitope. In some embodiments, the epitope is made by selecting at least one tumor associated antigen known to be expressed by a cancer, predicting the hydrophilicity and surface accessibility of a plurality of peptides having about 9 to about 12 consecutive amino acid residues of a tumor associated antigen expressed by the cancer, screening the peptides having a desired hydrophilicity and surface accessibility against antibodies that specifically bind the tumor associated antigen, and detecting the peptides which specifically bind the antibodies. In some embodiments, the cancer is melanoma, prostate cancer, non-small cell lung cancer, esophageal cancer, gastric cancer, hepatocellular carcinoma, bladder cancer, ovarian cancer, breast cancer, testicular cancer, prostate cancer, myeloma, small cell lung cancer or sarcoma. In some embodiments, the tumor associated antigen is NY-ESO-1 or XAGE-1b. In some embodiments, the epitope has a sequence of about 9 or more, preferably about 12 or more, consecutive amino acid residues of the tumor associated antigen. In some embodiments, the epitope (a) comprises at least 20 consecutive amino acid residues of SEQ ID NO:2; (b) consists essentially of at least 20 consecutive amino acid residues of SEQ ID NO:2; (c) consists of at least 20 consecutive amino acid residues of SEQ ID NO:2; (d) consists essentially of SEQ ID NO:3, SEQ ID NO:4, SEQ ID NO:5, SEQ ID NO:6, SEQ ID NO:7, SEQ ID NO:8, SEQ ID NO:9, or SEQ. ID NO:10; (e) consists of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (f) comprises at least 20 consecutive amino acid residues of SEQ ID NO:15; (g) consists essentially of at least 20 consecutive amino acid residues of SEQ ID NO:15; (h) consists of at least 20 consecutive amino acid residues of SEQ ID NO:15; (i) consists essentially of SEQ ID NO:16 or SEQ ID NO:17; or (j) consists of SEQ ID NO:16 or SEQ ID NO:17.

In some embodiments, the present invention provides a method for detecting, diagnosing, or monitoring a cancer in a subject which comprises contacting at least one epitope of the present invention with a sample obtained from the subject and detecting whether an antibody in the sample selectively binds the epitope. In some embodiments, the sample is a biological fluid such as urine, blood, plasma, serum, saliva, ascites and the like. In some embodiments, the cancer expresses NY-ESO-1, a NY-ESO-1 tumor associated antigen, XAGE-1b, or an XAGE-1b tumor associated antigen. In some embodiments, the cancer is melanoma, prostate cancer, non-small cell lung cancer, esophageal cancer, gastric cancer, hepatocellular carcinoma, bladder cancer, ovarian cancer, breast cancer, testicular cancer, prostate cancer, myeloma, small cell lung cancer or sarcoma. In some embodiments, a plurality of samples obtained from the subject are tested. In some embodiments, the plurality of samples are obtained before, during or after treating the cancer. In some embodiments, the regression, recurrence or progression of the cancer is determined by observing any change or difference in the antibody selectively binding the epitope from the plurality of samples.

In some embodiments, the present invention provides a purified polypeptide (a) comprising at least 20 consecutive amino acid residues of SEQ ID NO:2; (b) consisting essentially of at least 20 consecutive amino acid residues of SEQ ID NO:2; (c) consisting of at least 20 consecutive amino acid residues of SEQ ID NO:2; (d) consisting essentially of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (e) consisting of SEQ ID NO:3, SEQ ID NO:4, SEQ ID NO:5, SEQ ID NO:6, SEQ ID NO:7, SEQ ID NO:8, SEQ ID NO:9, or SEQ ID NO:10; (f) comprising at least 20 consecutive amino acid residues of SEQ ID NO:15; (g) consisting essentially of at least 20 consecutive amino acid residues of SEQ ID NO:15; (h) consisting of at least 20 consecutive amino acid residues of SEQ ID NO:15; (i) consisting essentially of SEQ ID NO:16 or SEQ ID NO:17; or (j) consisting of SEQ ID NO:16 or SEQ ID NO:17.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

FIGS. 1A-D are computer-aided predictions of B cell epitopes from NY-ESO-1.

FIG. 1A shows the predicted hydrophilicity of NY-ESO-1 which was calculated and plotted based on a window size of 17 amino acid residues.

FIG. 1B shows the predicted secondary structure of NY-ESO-1. Line 1=single lettered primary amino acid sequence; Line 2=predicted secondary structure: H (helix), E (strand), C (turn or loop); Line 3=8-class secondary structure prediction: H (alpha-helix), E (extended strand), B (beta-bridge), T (turn), S (bend), C (the rest).

FIG. 1C shows the predicted solvent (or surface) accessibility of NY-ESO-1 using a window size of 12 amino acid residues.

FIG. 1D shows the prediction for buried residues which was also performed to warrant the predicted epitopes scored high on surface accessibility and low as buried segments.

FIG. 2A shows the comparison of the sensitivity for Ab detection using ESO1-40 and NY-ESO-1. Sera from 11 melanoma subjects and 3 prostate cancer subjects with known NY-ESO-1 Ab were used.

FIG. 2B shows the comparison of the spontaneous Ab responses against NY-ESO-1 and ESO1-40 was shown in 92 prostate cancer subjects.

FIG. 2C shows the comparison of the spontaneous Ab responses against the NY-ESO-1 and ESO1-40 was shown in 101 NSCLC subjects.

DETAILED DESCRIPTION OF THE INVENTION

Figure 1C:
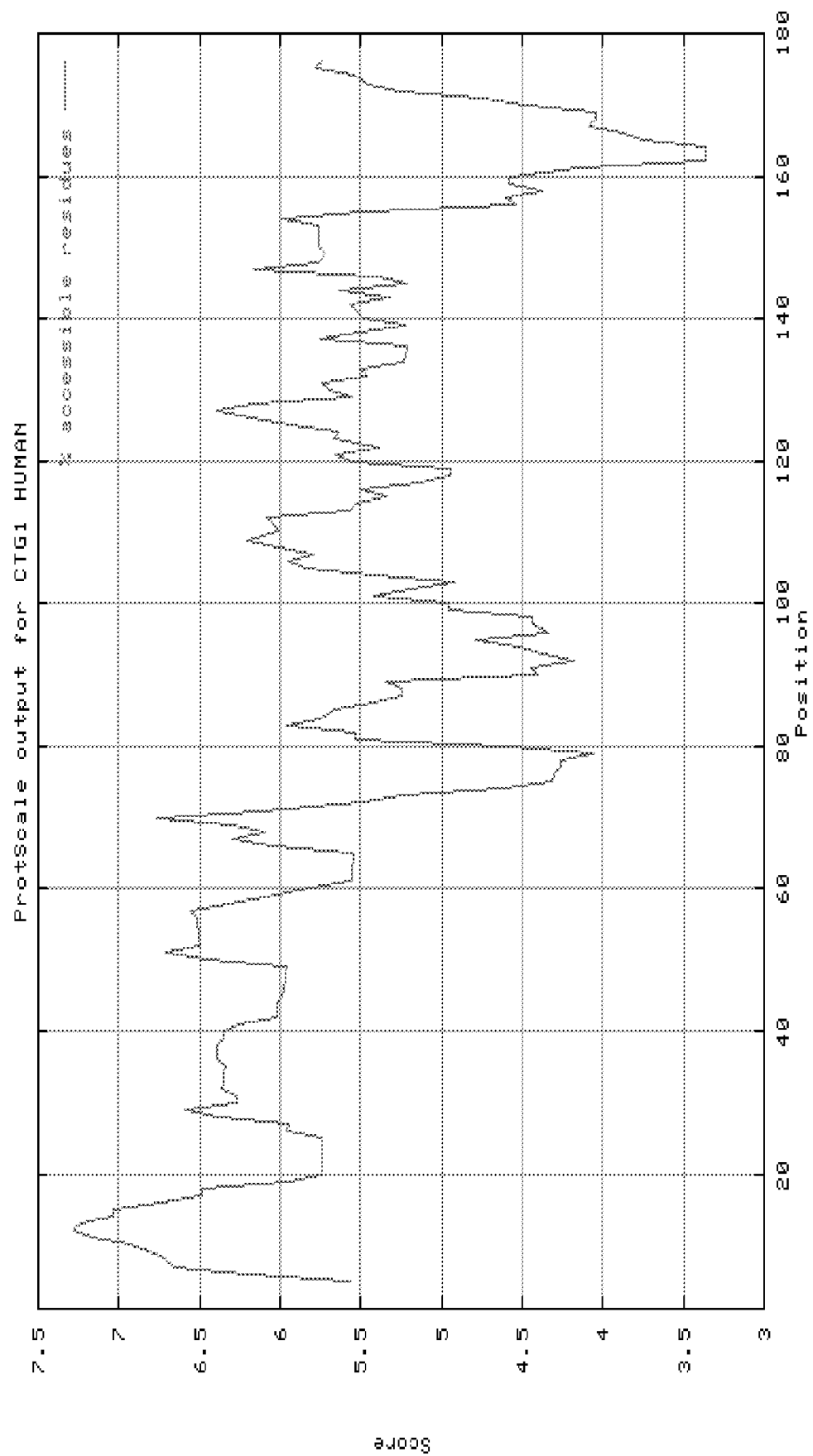

Most tumor associated antigens (TAA) do not react with more than about 5% to about 10% of allogeneic sera, with spontaneous antibody (Ab) responses against several TAA, such as p53, NY-ESO-1, and Her-2/neu, which are most frequently observed. See Zhang, J-Y, et al. (2003) Cancer Epidemiol Biomarkers Prey 12(2):136-143; and Stone, B, et al. (2003) Int J Cancer 104(1):73-84, which are herein incorporated by reference. Two main strategies are commonly used for the determination of serological profiles of SEREX-defined antigens: conventional serologic survey using phage lysate encoding specific TAA as the antigenic target and an ELISA-based approach using purified recombinant proteins as the antigenic target. The former approach requires large amounts of sera individually pre-adsorbed with E. coli phage lysates for the purpose of reduction of background; the latter is a robust method to screen relatively large numbers of subjects' sera. Previous studies even showed that many of the SEREX-defined TAA such as TOP2A, DDX5, and HOXB6 were difficult to express as recombinant proteins. In most recent studies, the feasibility to detect Ab using an array of purified recombinant proteins has been demonstrated. See Lagarkova, M A, et al. (2003) Immunol Lett 2003; 85(1):71-74, which are herein incorporated by reference. In order to exploit Ab responses against SEREX-defined TAA as potential biomarkers for cancer detection, prognosis, and prediction, a large panel of TAA that covers a broad range of subjects with a particular type of cancer is needed.

To circumvent the requirement of purifying individual protein, the present invention provides methods for identifying dominant B cell epitopes from TAA for detection of Ab against TAA and dominant B cell epitopes from TAA.

As used herein, "epitope" refers to a protein determinant capable of specific binding to an antibody. Epitopes usually comprise chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Identification of Epitopes
I. Obtain TAA for Given Cancer

First, at least one known TAA for a given cancer is identified and purified using methods known in the art. The TAA may be one known in the art or identified using methods known in the art such as SEREX. Desired TAA have antibodies that are only found in subjects having the given cancer, react with allogeneic Ab from other subjects having the given cancer, Ab recognition of the TAA is not the result of post-translational modification, and react with more than about 75% of the given cancer with insubstantial cross reactivity to other cancers. Nevertheless, less desirable TAA not meeting these criteria may be used according to the present invention.

2. Identify Seropositive Subjects for TAA

Then subjects diagnosed as having the given cancer and seropositive for the TAA are selected using methods known in the art and as described herein. Generally, sera from subjects diagnosed with the given cancer are collected. All serum samples are obtained from histologically confirmed subjects having the cancer. Serum samples are stored at −20° C. until they are analyzed.

Generally, sera samples from 100 cancer subjects and 40 healthy donors are obtained. Briefly, about 3 pmole of the TAA is diluted in 50 μl PBST (phosphate-buffered saline with 0.1% Tween 20) and plated to each well of a 96-well MaxiSorp plate (Nunc, Denmark). Control plates are coated with BSA at 200 ng/well. The plates are air-dried overnight at room temperature. All plates are blocked with 5% dry milk in PBST for at least 2 hours, washed, and loaded with 100 μl of diluted serum samples. Serum samples are diluted at 1:25, 1:125, and 1:625 with 3% dry milk in PBST. About 100 μl of each serum sample at the three different dilutions are loaded in duplicates onto the 2 plates coated with BSA and the target TAA, respectively.

After incubation, plates are washed, and loaded with the secondary antibody (goat anti-human IgG conjugated with horseradish peroxidase, Sigma, St. Louis, Mo.) followed by color development. Absorbance at 450 nm against BSA will be subtracted from that against the target TAA. A positive reaction is defined as an absorbance value that exceeds the mean value plus 3 times standard derivations of healthy donors at two of the 1:25, 1:125, and 1:625 dilutions.

3. Predict B Cell Epitopes Using Computer-Aided Algorithms

Basically, four parameters are important to determine the possibility for a linear peptide segment as an antigenic epitope recognized by Ab (Alix (1999) Vaccine 18(3-4): 311-314, which is herein incorporated by reference): (1) Secondary structure: Only the β-turns and coil conformations are considered to be favorable for antigenicity and thus the residues predicted in these conformations are most likely to be antigenically predicted. (2) Hydrophilicity: Only stretches of hydrophilic residues are considered favorable for direct contact with Ab. (3) Surface accessibility: Only residues that score high as exposed on the surface and low as buried in the interior have a favorable chance to directly interact with Ag. (4) Flexibility: The more flexible residues are more likely to be antigenic.

Two independent programs for the prediction of linear B cell epitopes from the TAA are used. One is the PHDsec program available to the public through Columbia University. See Rost (1996) Methods in Enzymology 266:525-539, which is herein incorporated by reference. PHDsec predicts the secondary structure of a protein by employing a system of neural networks rating at an expected average accuracy greater than about 72% for the three states helix, strand and loop. Evaluated on the same data set, PHDsec is rated at ten percentage points higher three-state accuracy than methods using only single sequence information, and at more than six percentage points higher than, e.g., a method using alignment information based on statistics. See Levin & Pascarella (1993) Protein Eng 6(8):849-854, which is herein incorporated by reference. PHDacc predicts per residue solvent accessibility from multiple sequence alignments, which is calculated by a neural network method rating at a correlation coefficient (correlation between experimentally observed and predicted relative solvent accessibility) of 0.54 cross-validated on a set of 238 globular proteins. Expressed in units of the difference between prediction by homology modelling (best method) and prediction at random (worst method), PHDacc is some 26 percentage points superior to a comparable neural network using three output states (buried, intermediate, exposed) and using no information from multiple alignments. See Rost & Sander (1994) Proteins 20:216-226, which is herein incorporated by reference.

Predictions are based on hydrophilicity plot, secondary structure, and accessibility to surface. Peptides that contain domains of proteins that score high in surface accessibility, low as buried segments and also possess flexible secondary structures will be identified. To reduce the possible bias by a single prediction program, a second independent program for peptide epitope prediction, the PEOPLE program developed by Alain Alix, Ph.D. at Reims University in France may also be used. See Alix (1999) Vaccine 18(3-4): 311-314, which is herein incorporated by reference. This program integrated prediction of surface accessibility and antigenicity of a protein segment based on primary structures.

The results by PHD program are presented as secondary structure prediction, scores of cell surface accessibility and possibilities as buried residues using a window of 12-amino acids. In contrast, the PEOPLE program results in a plot of the composite profile for potential antigenic peptides. Peptide segments from the top scored sequences may be selected and compared with the prediction from the PHD program. Once about a suitable number, about 10 to 20, candidate peptides at about 15 to 40 residues in length from the TAA are obtained, the candidate peptides are synthesized and purified to a purity of more than about 85%.

The peptides of the present invention may be made using methods known in the art including chemical synthesis, recombinant DNA methods, and solid phase synthesis. See e.g. Kelly & Winkler (1990) GENETIC ENGINEERING PRINCIPLES AND METHODS, vol. 12, J. K. Setlow ed., Plenum Press, NY, pp. 1-19; Merrifield (1964) J Amer Chem Soc 85:2149; Houghten (1985) PNAS USA 82:5131-5135; and Stewart & Young (1984) SOLID PHASE PEPTIDE SYNTHESIS, 2 ed. Pierce, Rockford, Ill., which are herein incorporated by reference. The peptides of the present invention may be purified using protein purification techniques known in the art such as reverse phase high-performance liquid chromatography (HPLC), ion-exchange or immunoaffinity chromatography, filtration or size exclusion, or electrophoresis. See Olsnes, S. and A. Pihl (1973) Biochem. 12(16):3121-3126; and Scopes (1982) PROTEIN PURIFICATION Springer-Verlag, N.Y., which are herein incorporated by reference.

In preferred embodiments, the polypeptides of the present invention are substantially purified. As used herein, a "substantially purified" compound refers to a compound that is removed from its natural environment and is at least about 60% free, preferably about 75% free, and most preferably about 90% free from other macromolecular components with which the compound is naturally associated.

As used herein, "isolated" refers to a polypeptide or peptide which is isolated from its native environment. For example, an isolated peptide is a one which does not have its native amino acids of the full length polypeptide flanking the N- or C-terminus or both. Thus, in the case of ESO1-40, and an isolated peptide comprising the ESO1-40 sequence would be one that may have non-native amino acids at its N- or C-terminus or both, but not amino acid residues 41-208 of NY-ESO-1 at its C-terminus. As used herein, "polypeptide" and "peptide" are used interchangeably to refer to at least two or more amino acids linked together.

4. Screen Candidate Peptides

The candidate peptides are then screened for reacting with sera from subjects identified as being seropositive for the TAA using methods known in the art. Only peptides that react with sera from the subjects seropositive for the TAA but not healthy donors will be identified as epitopes.

5. Analyze Epitopes for Frequency and Specificity and Relationship Between Ab Titers and TAA Expression 5A. Frequency and Specificity of Ab Against Epitope The epitopes that are validated as being reactive with sera from subjects seropositive for the TAA are complied as an epitope array, such as a 96-well plate. The array will then be tested for suitability for use as a diagnostic tool for assaying the given cancer in subjects. Generally, serum samples from 50 subjects diagnosed with having the cancer, 50 subjects identified as at high risk for the given cancer, and 50 healthy donors are obtained and assayed at various dilutions using the array. It is noteworthy that these serum samples will be obtained from subjects different from those used to identify the epitopes. The frequency and pattern of Ab responses will be recorded and analyzed using methods known in the art.

5B. Relationship Between Ab Titers and the TAA Expression

Methods known in the art may be used to determine the relationship between Ab titers against the TAA and TAA expression. Sera will be obtained after surgically removal of the primary tumor but prior to cancer therapy as well as 5 weeks and 13 weeks post the initial cancer therapy. Each subject will serve as his or her own control to find correlations between Ab titers, TAA expression in tumor specimens, and the clinical status of disease progression. Any relationships or patterns may be used to monitor and treat the cancer.

The arrays of the present invention may be further improved by removing epitopes that do not have a desirable frequency and specificity and adding epitopes identified as having desirable frequency and specificity.

The peptides of the present invention may be used to prepare antibodies against TAA by immunizing a suitable subject, e.g., rabbit, goat, mouse or other mammal with the polypeptide by methods known in the art. The antibodies may then be used to assay tissue samples for expressing the TAA. Antibodies of the present invention may be produced by methods known in the art. See e.g., Coligan (1991) CURRENT PROTOCOLS IN IMMUNOLOGY Wiley/Greene, N.Y.; and Harlow and Lane (1989) ANTIBODIES: A LABORATORY MANUAL, Cold Spring Harbor Press, NY; Stites, et al. (1986) BASIC AND CLINICAL IMMUNOLOGY 4th ed. Lange Medical Publications, Los Altos, Calif.; Goding (1986) MONOCLONAL ANTIBODIES: PRINCIPLES AND PRACTICE 2d ed. Academic Press, NY; and Kohler & Milstein (1975) Nature 256:495-497, which are herein incorporated by reference.

As used herein, "antibody" refers to immunoglobulin molecules and immunologically active portions that comprise an antigen binding site which specifically binds an antigen. Examples of immunologically active portions of immunoglobulin molecules include F(ab) and F(ab')$_2$ fragments which may be generated by treating the antibody with an enzyme such as pepsin. Polyclonal and monoclonal antibodies against the polypeptides of the present invention may be made by methods known in the art.

The present invention provides methods for assaying antibody titers against a TAA, such as NY-ESO-1. The assays may be used for evaluating whether a subject would be a suitable candidate for participating in a TAA specific vaccine trial and for assessing the immunologic and clinical responses of the treatment. As used herein, the term "assaying" is used

NY-ESO-1

As exemplified herein, NY-ESO-1 (SEQ ID NO:1) was used for identifying B cell epitopes for the following reasons: (1) NY-ESO-1 is a cancer/testis antigen, which is expressed in a number of human cancers including those of the esophageal, prostate, head and neck, lung, ovarian, breast, neuroblastoma, gastric, as well as melanoma, hepatocellular carcinoma (HCC), myeloma, and sarcoma. See Chen, Y T, et al. (1997) PNAS USA 94(5):1914-1918; Rodolfo, M, et al (2003) Cancer Res 63(20):6948-6955; and Lee, S Y, et al. (2003) PNAS USA 100(5):2651-2656, which are herein incorporated by reference. About 20% to about 30% of these cancers express the protein; and moreover, nearly about 40% to about 50% of the subjects with NY-ESO-1 expressing tumors develop antibodies against the protein. See Stockert, E, et al., (1998) J Exp Med 187(8):1349-1354, which are herein incorporated by reference. (2) Ab titers against NY-ESO-1 are driven by antigen expression of the endogenously arising tumor; and several studies have suggested that Ab titers against NY-ESO-1 correlated with advanced stages of the antigen-positive tumor in melanoma, transitional cell carcinoma, and prostate cancer. See Jager, E, et al (1999) Int J Cancer 84(5):506-510; Kurashige, T, et al. (2001) Cancer Res 61(12):4671-4674; and Nakada, T, et al., (2003) Cancer Immun 3:10, which are herein incorporated by reference. (3) Due to its high immunogenicity and broad expression in a variety of cancers, NY-ESO-1 has been chosen as the prototype for analysis in a number of cancer vaccine trials. See Davis, I D, (2004) PNAS USA 101(29):10697-10702, which is herein incorporated by reference.

The present invention provides dominant B cell epitopes from NY-ESO-1 and an epitope-based approach for measuring Ab that bypasses the requirement for purification of recombinant proteins. At least in previous studies involving subjects with prostate and transitional cell carcinoma, it has been indicated that NY-ESO-1 Ab are present mainly in subjects with advanced diseases. For example, NY-ESO-1 expression was observed in stage G1 and G2 transitional cell carcinomas and stage C prostate cancers, however, the Ab against NY-ESO-1 was only observed in stage G3 transitional cell carcinomas and stage D prostate cancers. See Kurashige, T, et al. (2001) Cancer Res 61(12):4671-4674; and Nakada, T, et al. (2003) Cancer Immun 3:10, which are herein incorporated by reference. Moreover, measurement of NY-ESO-1 Ab has been used to monitor NY-ESO-1 specific vaccine trials and to correlate with NY-ESO-1 specific T cell responses. See Jager, E, (2000) PNAS USA 97(9):4760-4765, which is herein incorporated by reference. Thus, the epitopes of the present invention may be used to monitor the progression and treatment of a cancer expressing NY-ESO-1 in subjects.

NY-ESO-1 also shares 94% and 88% identity with another cancer/testis antigen, LAGE-1 at the nucleotide and amino acid level respectively. See Lethe, B, et al. (1998) Int J Cancer 76(6):903-908, which is herein incorporated by reference. Both proteins have similar expression pattern and their expression is overlapping in most cases. Because of the high degree of homology between NY-ESO-1 and LAGE-1, serological assays using the full-length proteins were not able to reliably distinguish Ab against NY-ESO-1 and LAGE-1 in human sera. See Odunsi, K, et al. (2003) Cancer Res 63(18): 6076-6083, which is herein incorporated by reference. As provided herein, epitope ESO11-30 (SEQ ID NO:3) is identical between NY-ESO-1 and LAGE-1 and ESO 1-40 (SEQ ID NO:4) has only one amino acid difference between the two proteins, a Q for LAGE-1 and a R for NY-ESO-1 at the $6^{th}$ amino acid residue. These findings might explain why serological responses against these proteins are not distinguishable.

As provided herein, epitopes of the present invention may be used for detection of both NY-ESO-1 and LAGE-1 specific Ab in cancer subjects. In addition, Ab against NY-ESO-1 (both protein and peptide) are in general present in subjects with tumors expressing NY-ESO-1/LAGE-1 among the NSCLC and gastric cancer subjects in this study. The discrepancy, however, was seen in one NSCLC subject. Due to the heterogeneous expression pattern of NY-ESO-1 and other cancer/testis antigens, whether the sample used for RT-PCR was representative to the expression of NY-ESO-1/LAGE-1 in vivo was inconclusive. See Jungbluth, A A, et al. (2001) Int J Cancer 92(6):856-860, which is herein incorporated by reference.

Despite the advantages of the epitope approach for analyzing Ab against TAA, two major limitations exist. First, antibodies against less dominant epitopes and conformational epitopes of the TAA may be missed. As disclosed herein, the use of a full-length protein will cover more subjects than a fragment of the full-length protein alone. Second, NY-ESO-1 encodes a protein of 180 amino acid residues. For larger and more complex TAA, such as MAGE, SSX2, and CT7, it is likely that multiple peptide epitopes instead of one predominant epitope may be identified. Nevertheless, for these proteins, a step-wise peptide scanning strategy to reduce the total number of peptides needed for screening is provided herein. The fact that epitope ESO11-30 has the highest surface accessibility score according to the computer-assisted algorithm used in this study suggests that candidate peptides derived from large proteins can be screened according to the hierarchy of the predicted surface accessibility. Therefore, the present invention provides methods for identifying epitopes from TAA, including large TAA, comprising epitope prediction and step-wise screening.

XAGE-1b

Figure 3:
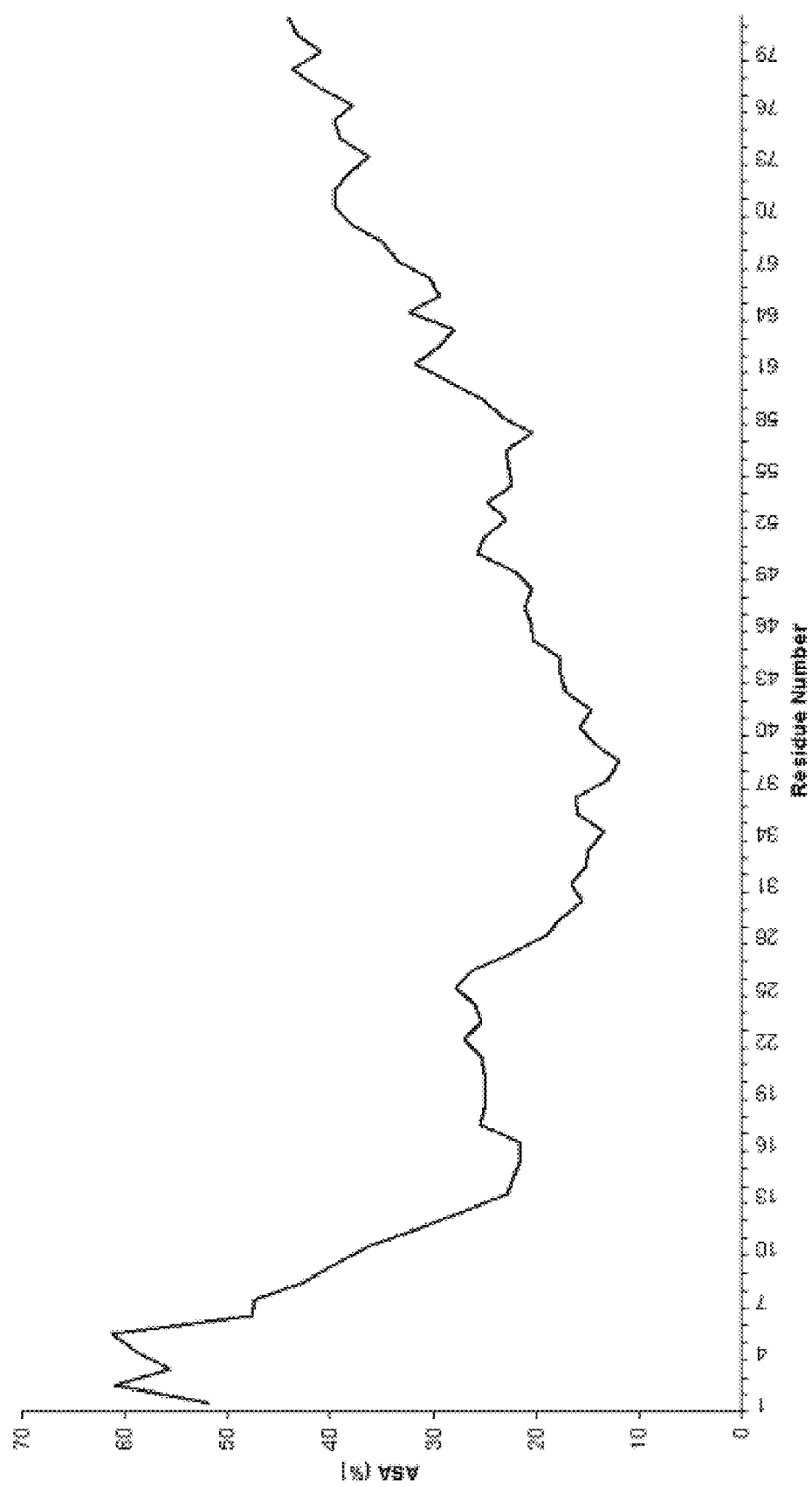
FIG. 3 shows a surface accessibility plot of XAGE-1b.
Figure 4:
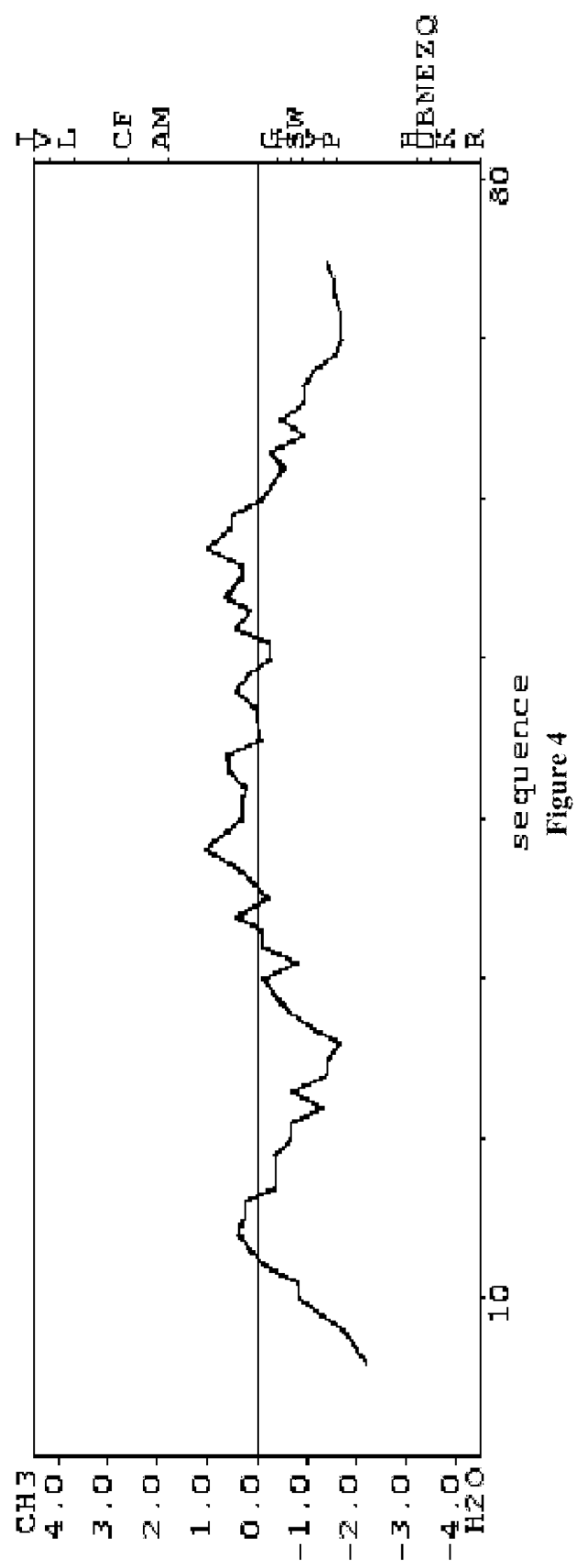
FIG. 4 shows a hydropathy plot of XAGE-1b using the Kyte-Doolittle method.

As exemplified herein, XAGE-1b (SEQ ID NO:15) was used for identifying B cell epitopes using methods similar to those for NY-ESO-1 disclosed herein. XAGE-1b is a TAA expressed in cancers of the lung, prostate, bladder, skin, and breast. Using the same method for predicting NY-ESO-1 epitopes as described herein, the values for accessible surface area (ASA) per residue in XAGE-1b were obtained and average ASA values spanning 12 residues were generated for a graphical understanding. See FIG. 3. The Kyte-Doolittle method provided hydropathy/hydrophilicity information for a 9 amino acid residue window as shown in FIG. 4. See Kyte, J, and Doolitle, R. (1982) J. Mol. Bio. 157:105-132, which is herein incorporated by reference. Regions with highest corresponding ASA (%) and lowest hydropathy values were predicted as XAGE-1b dominant B-cell epitopes.

Figure 5:
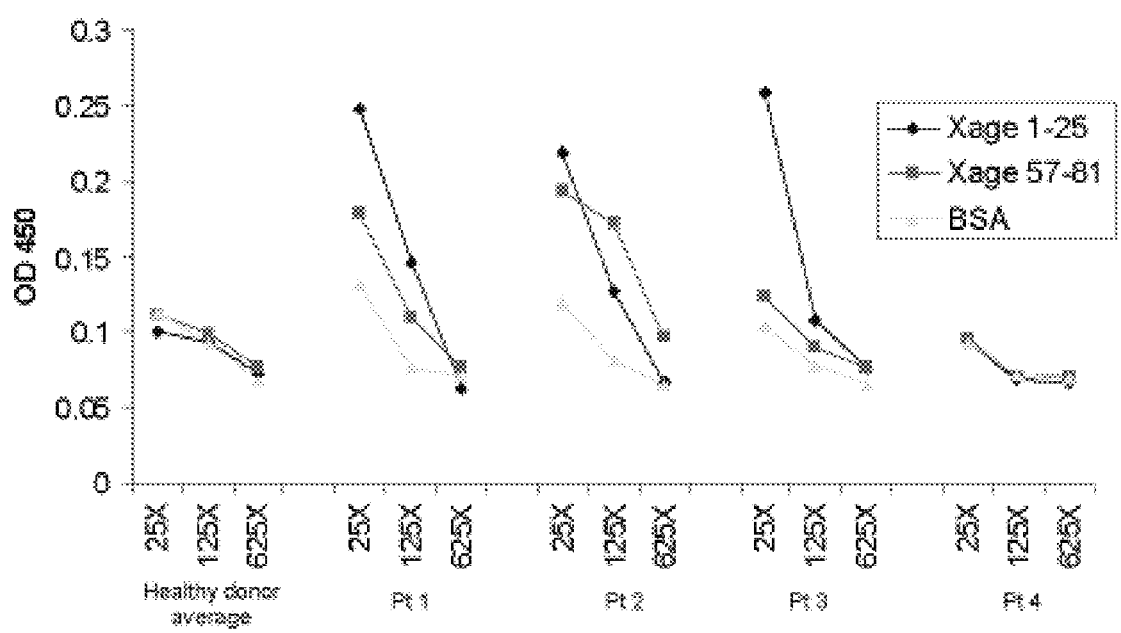
FIG. 5 shows Ab screening of seropositive subjects with Ab against XAGE-1b peptides and BSA. The average Ab titer of 8 healthy donors and selected NSCLC patients (3 out of 24 are positive: Patients 1-3: positive sera, Patient 4: representative of sera negative for peptide) were plotted.

ELISA was used to determine Ab against the predicted XAGE-1b epitopes. Plates were coated with 50 ng/well of peptides corresponding to the predicted epitopes, XAGE-1b residues 1-25 (SEQ ID NO:16) and XAGE-1b residues 57-81 (SEQ ID NO:17). Other plates were coated with a negative control (BSA). Non-small cell lung cancer (NSCLC) patient sera at 3 dilutions (1:25, 1:125, and 1:625) were used as the primary Ab. NSCLC was chosen as prototype due to proven expression of XAGE-1b. FIG. 5 shows the Ab titers of 8 healthy donors (average+3× standard deviation) and selected NSCLC subjects (Patients 1-3: positive sera, Patient 4: representative of sera negative for peptide) against XAGE-1b peptides (SEQ ID NO:15 and SEQ ID NO:16) and BSA. Background plate values (BSA) were subtracted from peptide plate values. Healthy donor sample values were used to determine the cutoff values for positive wells.

Figure 6A:
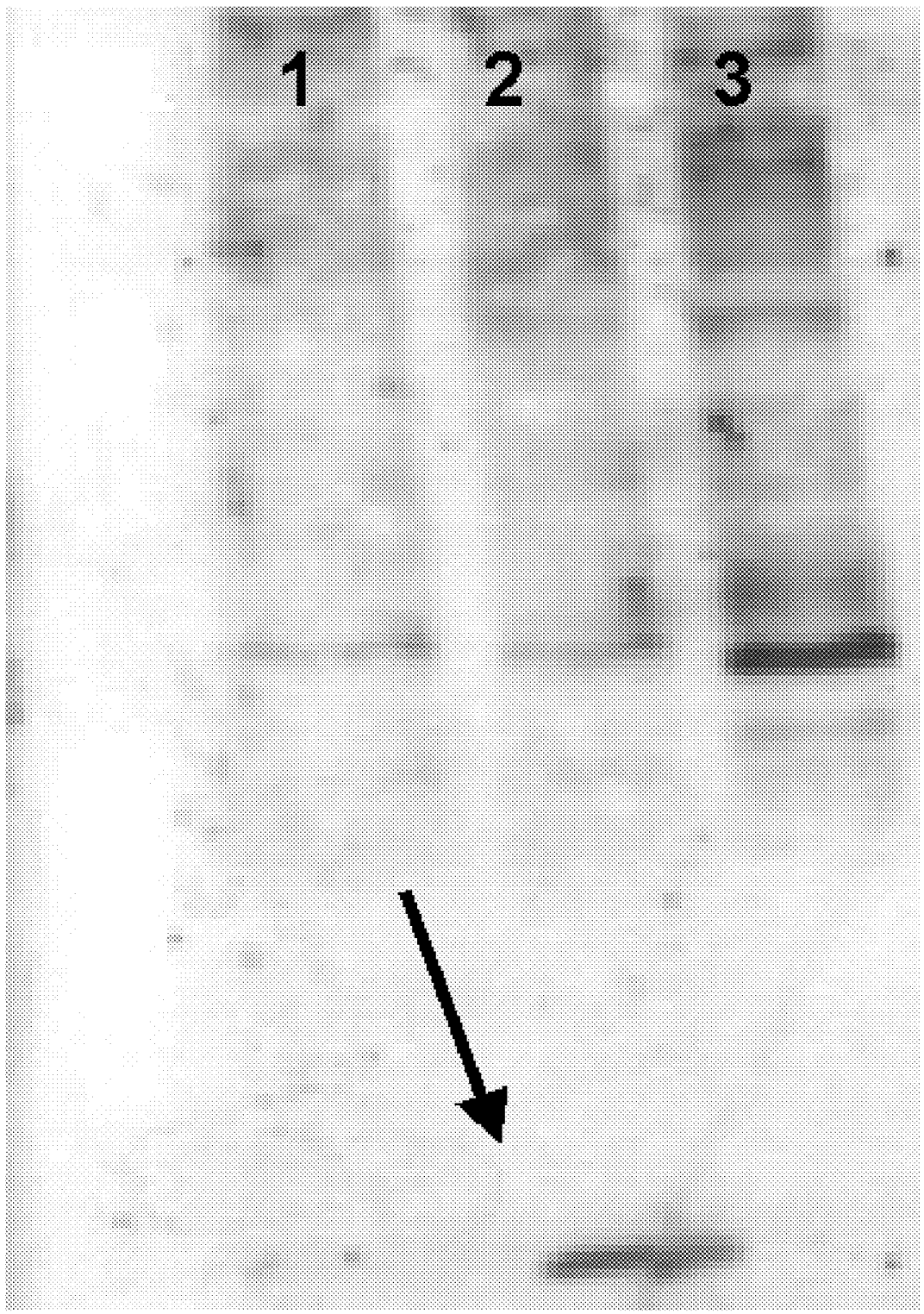
FIGS. 6A-C are Western Blots confirming XAGE-1b reactivity with the full-length XAGE-1b protein from seropositive subjects identified using the peptide screening approach herein. Lane 1: lysate from 293 cells transfected with GFP. Lane 2 (with denoted band): lysate from 293 cells transfected with a plasmid encoding XAGE-1b. Lane 3: LNCaP lysate, which is a prostate cancer line known to express XAGE-1b, although to a lesser degree.
Figure 6B:
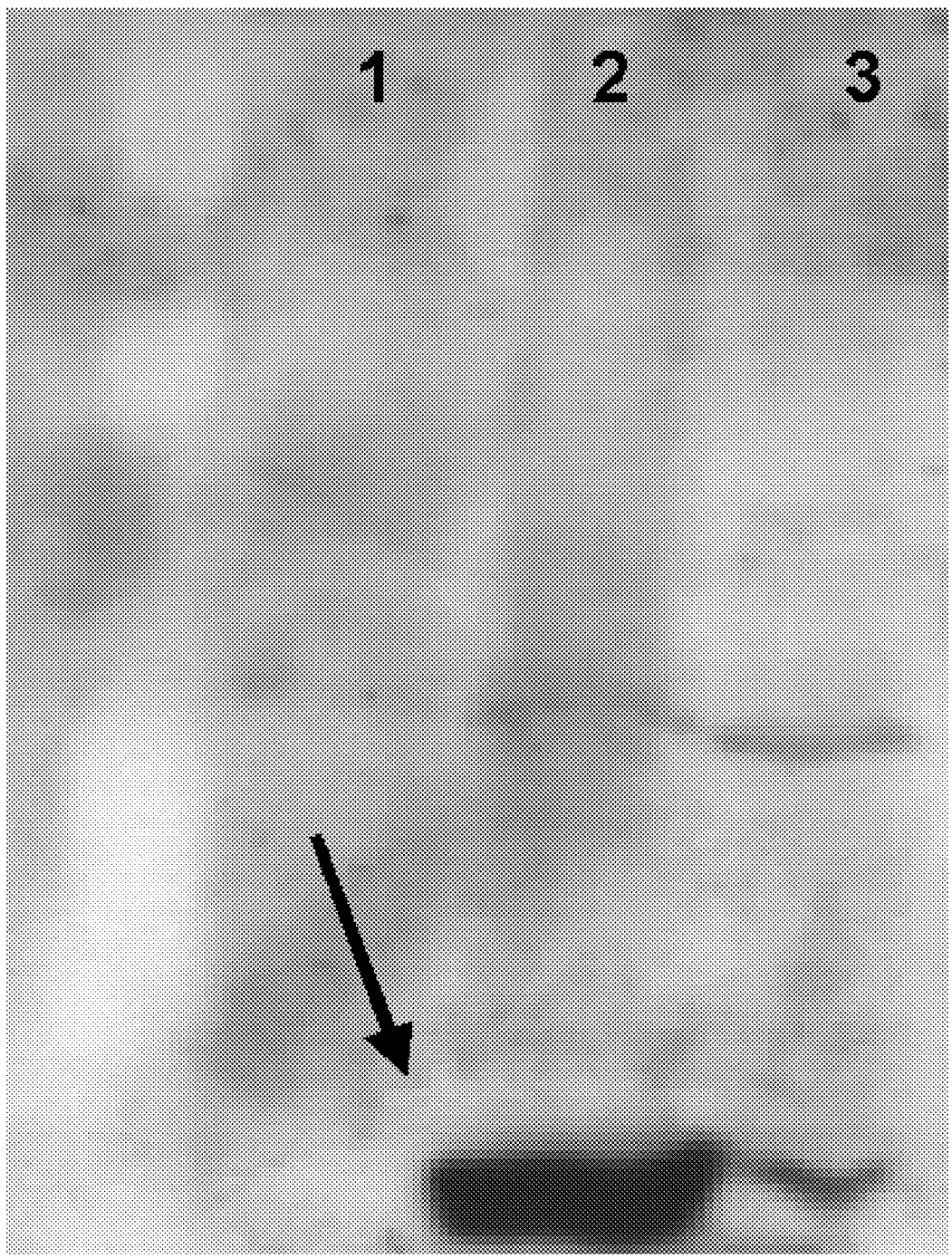
Figure 6C:
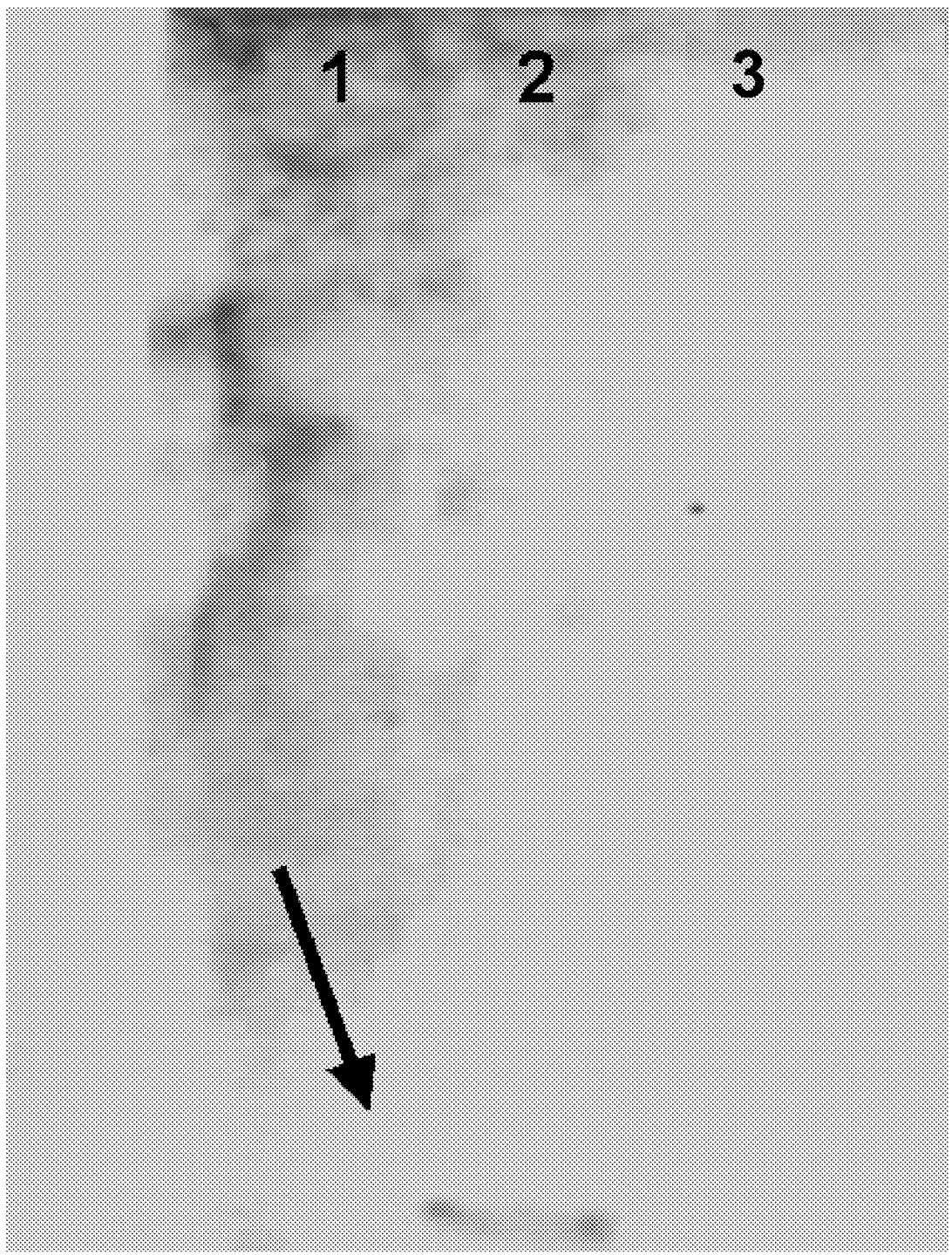

Sera reacting with the peptide epitopes were further validated by Western blot using methods known in the art. FIGS. 6A-C show Western blots which confirm Ab reactivity with the full-length XAGE-1b protein from seropositive subjects identified by assaying for Ab reactivity against the XAGE-1b peptides. Lane 1: lysate from 293 cells transfected with GFP. Lane 2 (with denoted band): lysate from 293 cells transfected with XAGE-1b. Lane 3: CL1 lysate, which is a prostate cancer line known to express XAGE-1b, although to a lesser degree.

As provided herein, subjects suffering from cancer, but not healthy subjects, exhibit significant Ab response against the XAGE-1b epitopes of the present invention, as well as, against the full length XAGE-1b protein. The frequency and sensitivity of the Ab response to XAGE-1b epitopes were comparable to that of the full length XAGE-1b protein. Therefore, the present invention provides epitopes that may be used for detecting antibodies against XAGE-1b in samples. Thus, the present invention also provides methods for detecting, diagnosing, and treating subjects suffering from a cancer that expresses XAGE-1b.

The present invention provides epitopes of TAA for a variety of cancers and libraries and arrays comprising the epitopes and methods of making and using the epitopes. As contemplated herein, the various cancers include melanoma, hepatocellular carcinoma, neuroblastoma, myeloma, various sarcomas, and cancers of the bladder, prostate, breast, ovary, head and neck cancer, lung, and testis and TAA for these cancers include melanoma, hepatocellular carcinoma, neuroblastoma, myeloma, various sarcomas, and cancers of the bladder, prostate, breast, ovary, head and neck cancer, lung, and testis.

The present invention also provides kits comprising at least one epitope according to the present invention. The kits may comprise reagents and buffers and assay devices or substrates. The epitopes according to the present invention may be used in methods for monitoring and treating a subject suffering from cancer.

An epitope of the present invention is capable of selectively binding an antibody raised against a TAA from which the epitope was obtained. In some embodiments, an epitope of the present invention is capable of selectively binding an antibody from a subject that was produced as an immune response against a TAA expressed by a cancer in the subject. As used herein, an "immune response" refers to a humoral or cellular response caused by exposure to an antigenic substance.

The epitopes of the present invention may be made by methods known in the art. The polypeptides of the present invention may be manually or synthetically synthesized using methods and devices known in the art. See e.g., Stewart and Young (1984) SOLID PHASE PEPTIDE SYNTHESIS, 2 ed. Pierce, Rockford, Ill., which is herein incorporated by reference. The epitopes of the present invention may be purified using protein purification techniques known in the art such as reverse phase high-performance liquid chromatography (HPLC), ion-exchange or immunoaffinity chromatography, filtration or size exclusion, or electrophoresis. See Olsnes, S. and A. Pihl (1973) Biochem. 12(16):3121-3126; and see e.g., Scopes (1982) PROTEIN PURIFICATION, Springer-Verlag, N.Y., which are herein incorporated by reference.

In some embodiments, the polypeptides of the present invention are substantially purified. As used herein, a "substantially purified" compound refers to a compound that is removed from its natural environment and is at least about 60% free, preferably about 75% free, and most preferably about 90% free from other macromolecular components with which the compound is naturally associated.

Alternatively, the polypeptides of the present invention may be made by recombinant DNA techniques known in the art. Thus, polynucleotides that encode the polypeptides of the present invention are contemplated herein. In preferred embodiments, the polynucleotides are isolated. As used herein "isolated polynucleotides" refers to polynucleotides that are in an environment different from that in which the polynucleotide naturally occurs.

A polypeptide of the present invention may be used to prepare antibodies against a given TAA by immunizing a suitable subject, e.g., rabbit, goat, mouse or other mammal with the polypeptide by conventional methods known in the art. Quantities of antibodies could be generated and then used detection reagents in immunological assays. Thus, the present invention also provides antibodies that are raised against or derived from the polypeptides of the present invention, and methods of using thereof.

Antibodies of the present invention may be produced by methods known in the art. See e.g., Coligan (1991) CURRENT PROTOCOLS IN IMMUNOLOGY. Wiley/Greene, N.Y.; and Harlow and Lane (1989) ANTIBODIES: A LABORATORY MANUAL, Cold Spring Harbor Press, NY; Stites, et al. (1986) BASIC AND CLINICAL IMMUNOLOGY. 4th ed. Lange Medical Publications, Los Altos, Calif.; Goding (1986) MONOCLONAL ANTIBODIES: PRINCIPLES AND PRACTICE. 2d ed. Academic Press, New York, N.Y.; and Kohler and Milstein (1975) Nature 256:495-497, which are herein incorporated by reference. Therapeutic antibodies may be produced specifically for clinical use in humans by conventional methods known in the art. See Chadd, H. E. and S. M. Chamow (2001) Curr. Opin. Biotechnol. 12:188-194 and references therein, all of which are herein incorporated by reference.

As used herein, "antibody" refers to immunoglobulin molecules and immunologically active portions that comprise an antigen binding site which specifically binds an antigen, such as ricin. Examples of immunologically active portions of immunoglobulin molecules include $F(ab)$ and $F(ab')_2$ fragments which may be generated by treating the antibody with an enzyme such as pepsin. Polyclonal and monoclonal antibodies against the polypeptides of the present invention may be made by methods known in the art.

The polypeptides, polynucleotides, or antibodies of the present invention may be administered, preferably in the form of pharmaceutical compositions, to a subject. Preferably the subject is mammalian, more preferably, the subject is human. Preferred pharmaceutical compositions are those comprising an epitope of the present invention or an antibody raised against an epitope of the present invention and a pharmaceutically acceptable vehicle.

The present invention also provides kits for conducting the assays described herein. Kits of the present invention comprise the provides polypeptides, polynucleotides, antibodies, or compositions of the present invention packaged together with other reagents used for conducting the assays described herein, devices for obtaining the samples to be assayed, devices for mixing the reagents and conducting the assays, instructional material, or a combination thereof. The diagnostic assays may be provided in the form of kits that may be used outside of a laboratory setting; such as in the field.

Prior art methods for monitoring progression and regression of cancer and responses to chemotherapy include computed tomography (CT) scanning, x-ray, sonogram, PET, and tissue biopsy. Traditional laboratory based analysis of biomarkers mainly focused on PSA, CA125, CEA, AFP, and the like. Unfortunately, these methods suffer from lack of sensitivity and specificity, expensiveness, and not suitable for large scale screening. Antibodies that specifically bind the epitopes of the present invention may be contacted with a biological sample, in vivo or in vitro, to determine whether the biological sample is cancerous, i.e. comprises a cell that expresses a TAA of a cancer that specifically binds the antibody. Alternatively, epitopes of the present invention may be contacted with a biological sample, in vivo or in vitro, to determine whether the biological sample contains antibodies that specifically bind the epitope, thereby indicating the subject from which the biological sample was obtained suffers from a cancer.

As used herein, "specifically binds" refers to a specific binding agent's preferential interaction with a given ligand over other agents in a sample. For example, a specific binding agent that specifically binds a given ligand, binds the given ligand, under suitable conditions, in an amount or a degree that is observable over that of any nonspecific interaction with other components in the sample. Suitable conditions are those that allow interaction between a given specific binding agent and a given ligand. These conditions include pH, temperature, concentration, solvent, time of incubation, and the like, and may differ among given specific binding agent and ligand pairs, but may be readily determined by those skilled in the art.

When an antibody specifically binds a given antigen, the antibody typically binds with an affinity of at least about $1 \times 10^7 M^{-1}$, and binds to the predetermined antigen with an affinity that is at least about two-fold greater than its affinity for binding to a non-specific antigen, e.g. BSA or casein, other than the predetermined antigen or a closely-related antigen. As used herein, the phrases "an antibody recognizing an antigen", "an antibody against an antigen", or "an antibody specific for an antigen" are used interchangeably with the phrase "an antibody which binds specifically to an antigen" and the like.

The following examples are intended to illustrate but not to limit the invention.

Example 1

Prediction of B-Cell Epitopes of NY-ESO-1 Using Computer-Assisted Algorithm

The prediction program PHDsec v 1.96 by Rost available at the Columbia University web site entitled "The PredictProtein Server" was used for predicting secondary structures of the NY-ESO-1 protein. See Rost (1996) Methods in Enzymology 266:525-539; and the web address is hypertext transfer protocol://cubic.bioc.columbia.edu/predictprotein/, which are herein incorporated by reference. The hydrophilicity/hydrophobicity analysis of NY-ESO-1 was calculated based on the Kyte-Doolittle method. See Kyte, J, and Doolitle, R. (1982) J. Mol. Bio. 157:105-132, which is herein incorporated by reference. A window of 12 amino acid residues was used to obtain the solvent accessibility plot using the PHDacc v 1.96 prediction program at "The PredictProtein Server". See Rost & Sander (1994) Proteins 20:216-226, which is herein incorporated by reference.

Figure 1D:
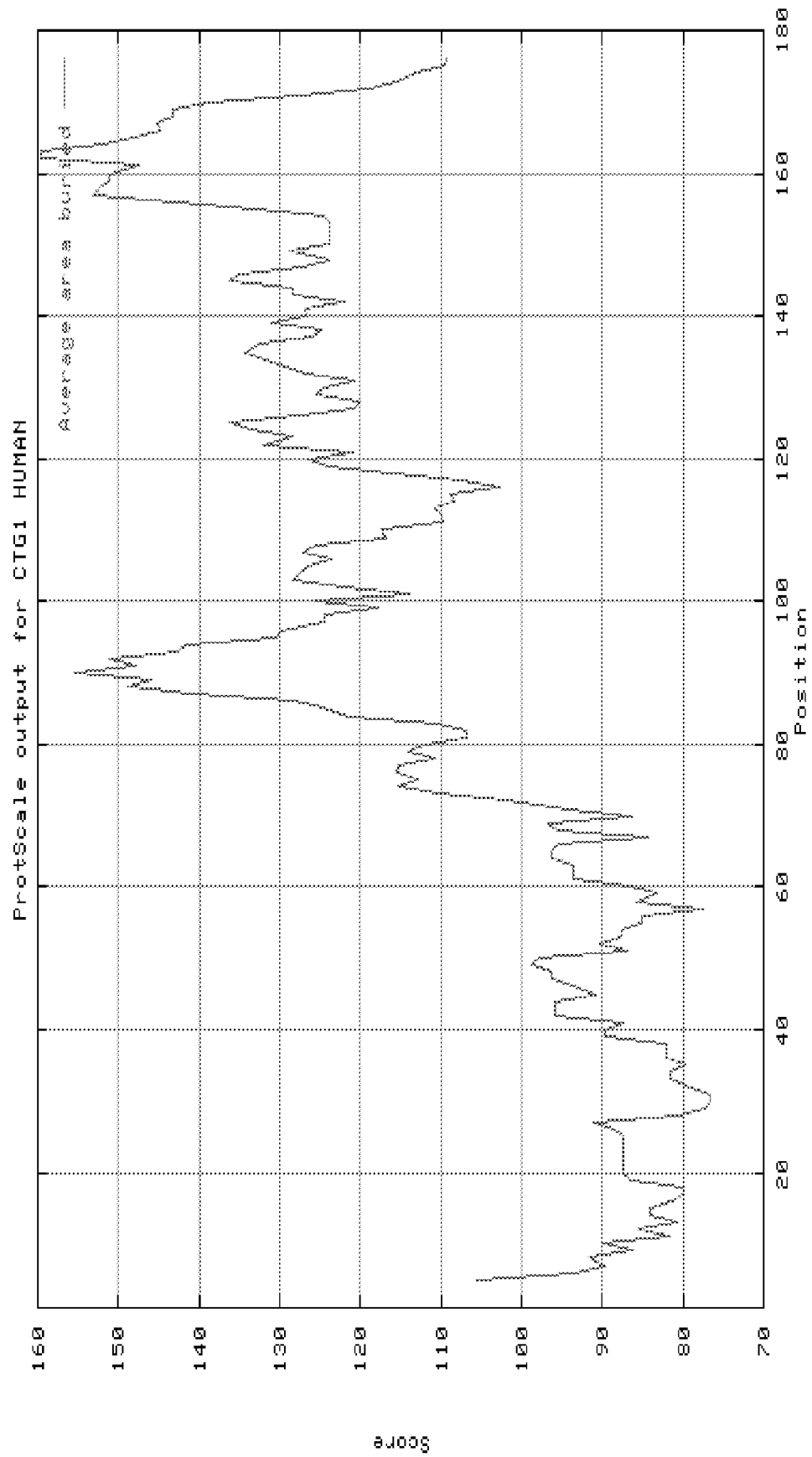

The 180-amino acid protein, NY-ESO-1 has a hydrophilic N-terminal domain and a hydrophobic C-terminal domain based on hydropathical profiles predicted using the Kyte-Doolittle method. See Kyte, J, and Doolitle, R. (1982) J. Mol. Bio. 157:105-132, which is herein incorporated by reference. The predicted hydrophilicity is shown in FIG. 1A. The N-terminal hydrophilic domain is composed of the first 74 amino acids. It is known that linear epitopes of small sequence segments are usually peptides conferring relatively loose conformations, such as the beta-turn and coil conformations. See Alix, A J (1999) Vaccine 18(3-4):311-314, which is herein incorporated by reference. Thus, the secondary structure of NY-ESO-1 was predicted using prediction program PHDsec. FIG. 1B showed that the N-terminal hydrophilic domain (amino acids 1 to 74) of NY-ESO-1 primarily conferred a flexible loop or turn conformation while the C terminal conferred more restrained helix conformation. Using the PHDacc program, the sequences exposed on the surface of the NY-ESO-1 protein were predicted as well as sequences buried to the interior of the protein. See FIGS. 1C and 1D, respectively. Essentially, the N-terminal hydrophilic domain was predicted to be exposed on the surface of the protein, which was accessible to the solvent while the C-terminal domain was buried in the interior of the protein. Therefore, the N-terminal may have direct contact with immunoglobulin molecules on the surface of a plasma B cell and contain B-cell epitopes recognized by Ab present in sera of subjects.

To identify the linear fragments of NY-ESO-1, which were recognized by serum-derived antibodies against NY-ESO-1, the recognition of recombinant ESO1-74 protein was tested and confirmed using a positive serum sample from a melanoma subject recognizing the full-length protein (data not shown). Since most linear epitopes consisted of at least 7 amino acid residues, a window of 12 amino acid residues was used to obtain the solvent accessibility plot. See FIGS. 1C and 1D. According to the prediction, synthesized peptides of 20 amino acid residues with 15-amino acid overlaps between every two consecutive peptides were used to identify the B cell epitopes derived from NY-ESO-1.

Example 2

Preparation of Recombinant Proteins and Synthetic Peptides

Recombinant NY-ESO-1 protein and the truncated ESO1-74 protein containing the first 75 amino acids were purified from bacteria as previously reported. See Zeng, G, et al. (2000) J Immunol 165(2):1153-1159, which is herein incorporated by reference. Synthetic peptides used in this study were made using a solid-phase method on a peptide synthesizer (Gilson Co. Inc., Worthington, Ohio) at the Surgery Branch of the National Cancer Institute and at Bio-synthesis, Inc. However, it is noted that peptides of the present invention may be obtained by other methods known in the art. The molecular weights of individual peptides were evaluated by mass spectrometry to confirm the identity of each peptide (Bio-synthesis, Inc., Lewisville, Tex.). Peptides were resuspended in DMSO solution at about 10 to about 20 mg/ml and stored at about −20° C. until use.

Example 3

Detection of NY-ESO-1 Antibodies in Serum Samples

Sera from subjects diagnosed prostate cancer were collected at the UCLA medical center. Sera from subjects diagnosed with gastric cancer, NSCLC, esophageal cancer, and HCC were collected at the Beijing Cancer Hospital, Peking University Medical Center, China. Sera from subjects diagnosed with melanoma and healthy donors were obtained from the Blood Bank at the Clinical Center of the National Institutes of Health. All serum samples were from histologically confirmed subjects having cancer; however, the clinical stages of each cancer varied from subject to subject. Serum samples were stored at −20° C. until they were analyzed.

To prepare antigen-coated plates, 50 ng/well of purified NY-ESO-1 protein or 10 ng/well of synthetic peptides were diluted in 50 μl PBS and were adsorbed onto a 96-well Max-iSorp plate (Nunc, Denmark) overnight at room temperature. Control plates were coated with BSA at 150 ng/well. Plates were blocked with 5% fetal bovine serum in PBST (PBS plus 0.05% Tween-20) for at least 2 hours, washed with PBST, and loaded with 100 μl of diluted serum samples. All serum samples were diluted at 1:25, 1:125, and 1:625 with PBST containing 5% fetal bovine serum unless otherwise specified. Each sample at the three different dilutions was loaded onto pre-coated ELISA plates. After a 2-hour incubation at room temperature, plates were washed, and loaded with secondary antibodies (goat anti-human immunoglobulin conjugated with horseradish peroxidase, Sigma Co., St. Louis, Mo.) diluted with 5% fetal bovine serum in PBST. Plates were developed after a one-hour incubation, and absorbance at 450 nm was read by using an ELISA reader. The cut-off value was defined as the mean optimal density (OD) value plus 3 times standard derivations of healthy donors. If an OD value against NY-ESO-1 or the peptide exceeded the cut-off at 2 of the 3 dilutions, the sample was regarded as positive.

Previously, 11 out of 88 subjects diagnosed with melanoma were identified as having class-switched Ab against the NY-ESO-1 protein. See Zeng, G, et al. (2000) J Immunol 165(2): 1153-1159; and Zeng, G, et al. (2001) PNAS USA 98(7): 3964-3969, which are herein incorporated. Positive serum samples form these subjects were diluted at various concentrations and applied to ELISA plates coated with 12 candidate peptides consisting of 20 amino acid residues that span the entire surface-exposed domain of NY-ESO-1. As shown in Table 1, 10 out of the 11 serum samples reacted with a single 20-mer peptide, ESO11-30, which may represent the core of a dominant B cell epitope.

dominant B-cell epitopes recognized by NY-ESO-1 specific Ab present in subjects suffering from cancer. ESO1-40 is exemplified herein for measuring Ab against the NY-ESO-1 antigen.

Figure 2A:
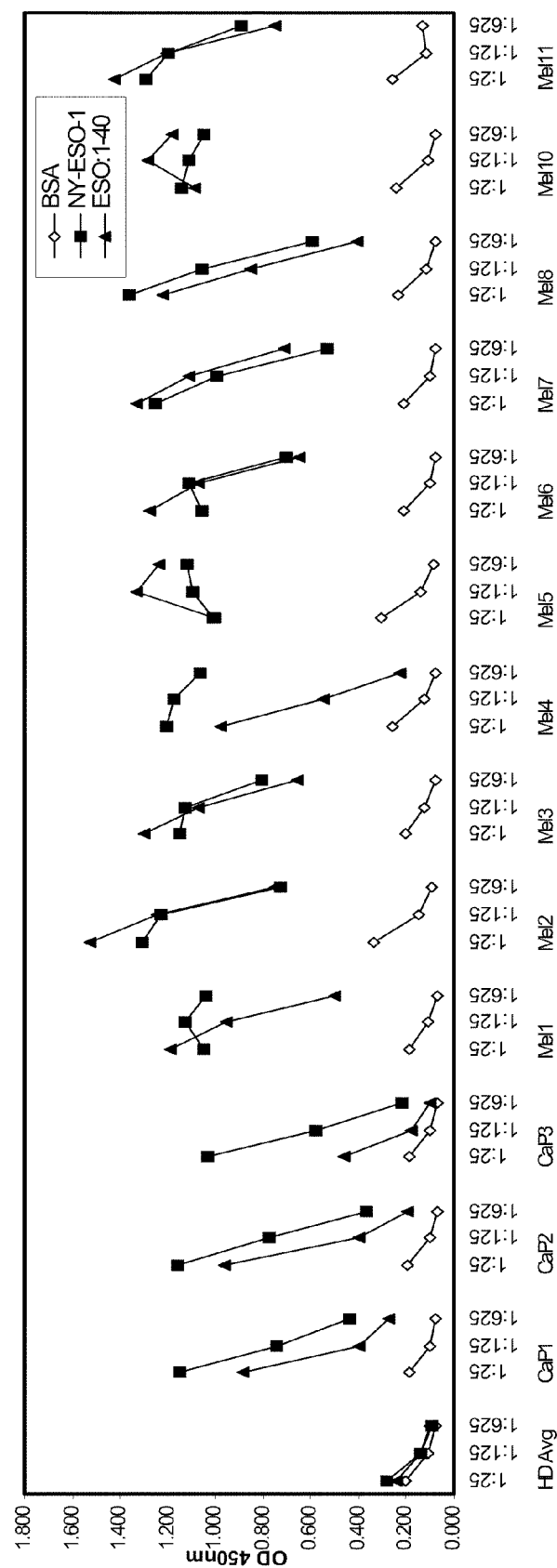
FIGS. 2A-C shows the detection of NY-ESO-1 Ab using ESO1-40 as an epitope representative of those according to the present invention. In all experiments, sera from at least 8 healthy donors (HD) were used to obtain the cut-off value (red dash), which was the average of OD plus three-fold of the standard derivation. OD against BSA was subtracted from the OD values against NY-ESO-1 and ESO1-40.

To determine whether sera reacted with ESO1-40 with a similar sensitivity as the NY-ESO-1, titration experiments were performed using known positive sera samples. First, one melanoma subject and two prostate cancer subjects with NY-ESO-1 specific Ab were randomly selected for comparing activities against ESO1-40 and NY-ESO-1. Interestingly, sera samples reacted similarly with NY-ESO-1 and ESO1-40 only when fetal bovine serum (FBS) was used as the blocking agent. When 5% milk was used as the blocking agent, the apparent Ab titers against the peptide decreased dramatically (data not shown). Therefore, 5% FBS was used as the blocking agent to compare the sensitivity for Ab detection against the same number of NY-ESO-1 and ESO1-40 molecules used to coat the plates. All ten positive sera from melanoma subjects (Table 1) and 3 positive sera from prostate cancer subjects reacted strongly against the peptide as well as the recombinant protein. In most cases (⅔ prostate cancer subjects and 9/10 melanoma subjects), ESO1-40 was as sensitive as NY-ESO-1 for measuring Ab responses at the various dilutions tested in the experiment. See FIG. 2A.

Figure 2B:
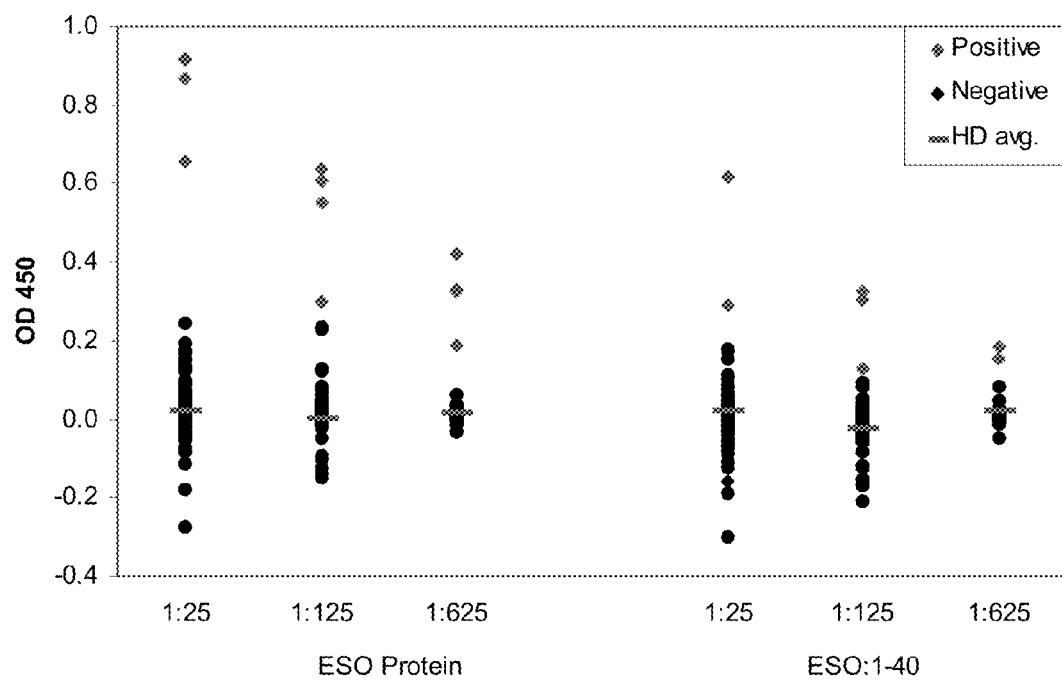

To demonstrate the feasibility of using a B cell epitope of the present invention as a suitable substitute for NY-ESO-1, ESO1-40 was used to measure Ab against NY-ESO-1 in subjects with cancers other than melanoma. First, the feasibility of using ESO1-40 to measure Ab against NY-ESO-1 in prostate cancer subjects was evaluated. Sera from 92 prostate cancer subjects were diluted at 1 to 25, 1 to 125, and 1 to 625, and used in an ELISA experiment using methods known in the art. As shown in FIG. 2B, four serum samples from prostate cancer subjects were positive against the full-length protein. Three of the 4 serum samples also reacted with ESO1-40 based on the criteria described herein. It was noteworthy that the secondary antibody used in this experiment and the following experiments involving non-melanoma subjects was against all isotypes of immunoglobulins, not only IgG, as sera from melanoma subjects was used. Comparing the average OD values and standard derivations of the OD from serum samples against NY-ESO-1 and ESO1-40, ELISA performed on ESO1-40-coated plates resulted in standard derivations that were lower than those of NY-ESO-1. This may indicate

TABLE 1

Detection of Ab against predicted NY-ESO-1 specific B cell epitopes from 11 melanoma subjects.

| | OD$_{450}$ against the following 20-mer peptides derived from NY-ESO-1* | | | | | | | | | | | |
|---|---|---|---|---|---|---|---|---|---|---|---|---|
| Subject | ESO 1-20 (SEQ ID NO: 5) | ESO 6-25 (SEQ ID NO: 6) | ESO 11-30 (SEQ ID NO: 3) | ESO 16-35 (SEQ ID NO: 7) | ESO 21-40 (SEQ ID NO 8) | ESO 26-45 (SEQ ID NO: 9) | ESO 31-50 (SEQ ID NO: 10) | ESO 36-55 | ESO 41-60 | ESO 46-65 | ESO 51-70 | ESO 56-75 |
| LD | 0.068 | 0.634 | 0.489 | 0.05 | 0.049 | 0.037 | 0.039 | 0.039 | 0.034 | 0.035 | 0.027 | 0.034 |
| TE | 0.245 | 0.26 | 0.169 | 0.146 | 0.104 | 0.026 | 0.028 | 0.025 | 0.041 | 0.032 | 0.08 | 0.113 |
| CJ | 0.1 | 0.175 | 0.382 | 0.369 | 0.332 | 0.043 | 0.055 | 0.06 | 0.081 | 0.058 | 0.055 | 0.185 |
| BE | 0.027 | 0.06 | 0.038 | 0.02 | 0.022 | 0.019 | 0.022 | 0.021 | 0.022 | 0.024 | 0.018 | 0.023 |
| KF | 0.032 | 0.057 | 0.081 | 0.071 | 0.078 | 0.025 | 0.027 | 0.026 | 0.025 | 0.028 | 0.026 | 0.024 |
| FJ | 0.123 | 0.517 | 0.467 | 0.433 | 0.36 | 0.035 | 0.034 | 0.035 | 0.035 | 0.031 | 0.036 | 0.04 |
| AC | 0.028 | 0.582 | 0.502 | 0.196 | 0.177 | 0.545 | 0.179 | 0.031 | 0.032 | 0.032 | 0.042 | 0.03 |
| DA | 0.037 | 0.054 | 0.176 | 0.042 | 0.043 | 0.039 | 0.041 | 0.043 | 0.044 | 0.034 | 0.046 | 0.038 |
| BF | 0.048 | 0.269 | 0.198 | 0.096 | 0.101 | 0.1 | 0.079 | 0.03 | 0.075 | 0.032 | 0.04 | 0.045 |
| BL | 0.043 | 0.064 | 0.054 | 0.034 | 0.029 | 0.013 | 0.228 | 0.034 | 0.016 | 0.021 | 0.026 | 0.026 |
| CT | 0.03 | 0.04 | 0.108 | 0.029 | 0.032 | 0.068 | 0.037 | 0.022 | 0.021 | 0.026 | 0.037 | 0.101 |

*Peptides containing 20 amino acid residues at a final amount of 10 ng/well were used to coat 96-well maxi-sorb plates. ELISA was performed using 1 to 250 diluted serum samples from all 11 subjects who had Ab against NY-ESO-1 as previously reported. OD$_{450}$ values that were at least three fold above the background (average of three lowest OD values) are boldface in the table and were considered positive for recognition of the predicted epitopes.

All 11 sera contained IgG Ab reacting with at least one of the four peptides in close context, i.e. ESO6-25, ESO11-30, ESO16-35, and ESO21-40. Recognition of two other peptides, ESO51-70 and ESO56-75 was also observed in 1 and 3 subjects, respectively. Therefore, peptides comprising at least 20 consecutive amino acid residues of amino acid residues 1-50 of NY-ESO-1, ESO1-50 (SEQ ID NO:2), represent that using epitopes of the present invention yields lower background than that using NY-ESO-1.

Figure 2C:
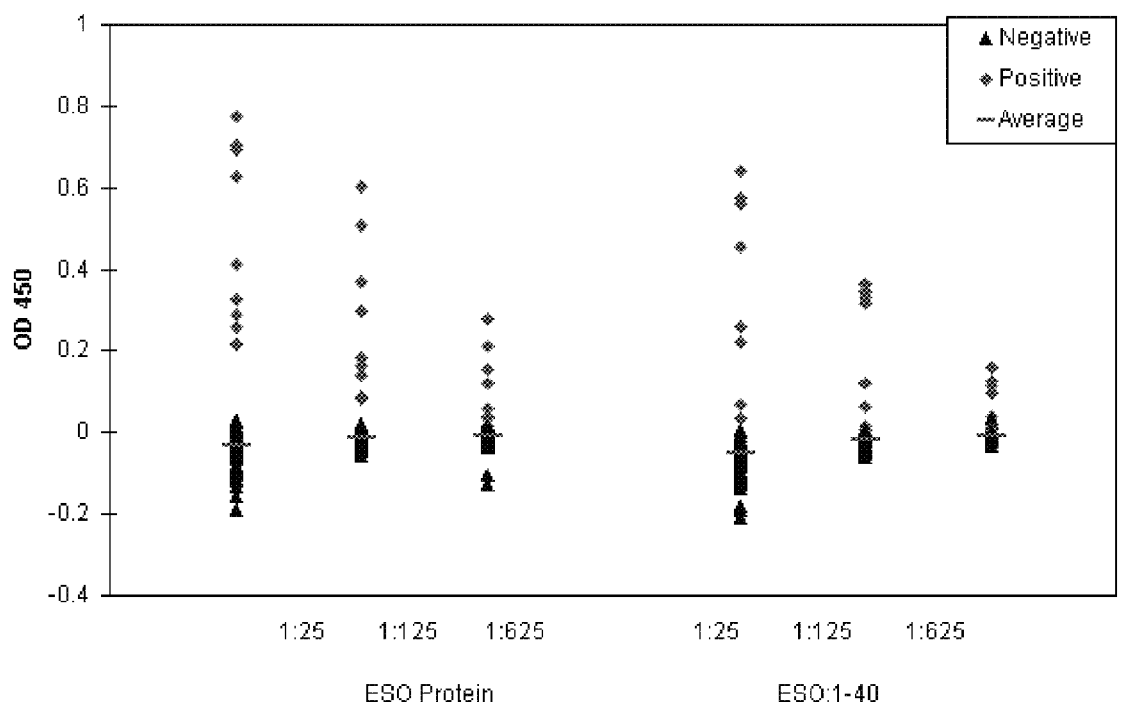

ESO1-40 was also compared with NY-ESO-1 for detection of NY-ESO-1 Ab in subjects with gastric cancer, NSCLC, esophageal cancer, and HCC. In each experiment, sera from at least 8 healthy donors were used as controls to obtain the cut-off value for defining positive reactions. As shown in FIG. 2C, 9 of 101 subjects with NSCLC had Ab against NY-ESO-1. Seven of the 9 Ab positive subjects also reacted with ESO1-40. In addition to prostate cancer and NSCLC subjects, 8 of the 113 gastric cancer subjects showed Ab responses against NY-ESO-1. The results are summarized in Table 2 as follows:

TABLE 2

Frequency of antibody responses against NY-ESO-1 protein and the ESO1-40 peptide in various cancer subjects

| Cancer Types | Total number of sera | NY-ESO-1 (+) | ESO1-40 (+) |
|---|---|---|---|
| Melanoma | 88 | 11 (11) | 11 (11) |
| Gastric Cancer | 113 | 8 (5) | 5 (5) |
| HCC | 101 | 9 (6) | 7 (6) |
| NSCLC | 101 | 9 (7) | 7 (7) |
| Esophageal Cancer | 48 | 8 (3) | 3 (3) |
| Prostate Cancer | 92 | 4 (3) | 3 (3) |

Numbers in parenthesis represent serum samples that are positive against both the NY-ESO-1 and ESO1-40. The experiments were repeated three times with similar results obtained in order to conclude the number of positive sera.

Five of the 8 seropositive subjects reacted with ESO1-40. Nine out of 101 HCC sera reacted with NY-ESO-1, and detected 7 positive sera reacting with ESO1-40. Six of the sera reacted with NY-ESO-1 and ESO1-40. Eight of 48 serum samples from esophageal cancer subjects reacted with NY-ESO-1. However, only 3 of the 8 subjects reacted with ESO1-40, indicating a lower frequency of Ab responses against ESO1-40 than NY-ESO-1 for esophageal cancer subjects. The overall frequency of spontaneous NY-ESO-1 Ab detected with NY-ESO-1 and ESO1-40 in the above cancer types is provided in Table 2. In summary, ESO1-40 represented a dominant epitope that is suitable for measuring NY-ESO-1 Ab in the majority of cancer subjects.

Since ESO1-40-coated plates often had lower background, whether increasing the quantity of antigenic targets on the plate might enhance the measurement of Ab was investigated. ELISA plates coated with increasing amount of peptide were compared at 10 ng/well, 20 ng/well, and 40 ng/well, no significant difference was observed in the absorbance of the reaction (data not shown).

Therefore, the epitopes of the present invention may be used to assay NY-ESO-1 Ab in subjects for determining whether a subject is suffering from a cancer including melanoma, prostate cancer, gastric cancer, NSCLC, and HCC.

Example 4

RT-PCR Analysis of NY-ESO-1 and LAGE-1 Expression in Fresh Tumor Samples

Trizol™ reagent (Invitrogen, Carlsbad, Calif.) was used to extract total RNA from freshly isolated tumor specimens using methods known in the art. The first cDNA strand was synthesized from 2.0 μg of total RNA by the Superscript First-Strand Synthesis System (Invitrogen, Carlsbad, Calif.) for RT-PCR. Presence of the mRNA encoding NY-ESO-1 and LAGE-1 was detected by polymerase chain reaction (PCR) using AmpliTaq Gold (ABI, Norwark, Conn.) using methods known in the art. The primers for NY-ESO-1 and LAGE-1 are as follows:

```
                                        (SEQ ID NO: 11)
ESO1-F: 5'-CAG GGC TGA ATG GAT GCT GCA GA-3'

(SEQ ID NO: 12)
ESO1-R: 5'-GCG CCT CTG CCC TGA GGG AGG-3'

(SEQ ID NO: 13)
LAGE1-F: 5'-CTG CGC AGG ATG GAA GGT GCC CC-3'

(SEQ ID NO: 14)
LAGE1-R: 5'-GCG CCT CTG CCC TGA GGG AGC-3'
```

The integrity and quantity of the cDNA were determined by the amplification of glyceraldehyde-3-phosphate dehydrogenase mRNA using methods known in the art. Positive and negative controls were included in each PCR analysis experiment.

Previous studies have provided evidence that the development of NY-ESO-1 Ab in cancer subjects is driven by the expression of the antigen in cancer cells. See Jager, E, et al. PNAS USA (2000) 97(9):4760-4765, which is herein incorporated by reference. As provided herein, the expression of NY-ESO-1 and LAGE-1 antigen in the tumor specimens from NSCLC and gastric cancer subjects who had a positive Ab reaction was analyzed. The results are summarized in Table 3 as follows:

TABLE 3

Expression of the NY-ESO-1 and LAGE-1 antigens in subjects with Ab against NY-ESO-1 and/or ESO1-40

| | Ab against the NY-ESO-1 (ESO1-40) | NY-ESO-1 expression | LAGE-1 expression |
|---|---|---|---|
| NSCLC subjects | | | |
| L30 | + (+) | + | + |
| L47 | + (+) | + | − |
| L50 | + (+) | + | + |
| L53 | + (+) | NA | NA |
| L59 | + (+) | + | + |
| L62 | + (−) | NA | NA |
| L73 | + (+) | NA | NA |
| L75 | + (−) | + | + |
| L98 | + (+) | − | − |
| Gastric cancer subjects | | | |
| G23 | + (+) | + | + |
| G32 | + (−) | + | + |
| G45 | + (+/−) | + | + |
| G46 | + (−) | + | + |
| G47 | + (+) | + | + |
| G74 | + (+) | NA | NA |
| G84 | + (+) | − | + |
| G100 | + (+) | + | + |

NA = tumor specimens not available for analysis.

Due to limitations of available fresh tumor specimens, Ab+-subjects with other cancers were not analyzed. Five of the 9 Ab+-NSCLC subjects had NY-ESO-1 and/or LAGE-1 expression in their tumor specimens; 3 NSCLC subjects were not analyzed due to unavailable tumor specimens; 1 subject was not evident of either NY-ESO-1 or LAGE-1 expression using the RT-PCR approached employed in the experiment. Except for one gastric cancer subject whose tumor specimen was unavailable for analysis, all remaining 6 Ab+-subjects had NY-ESO-1 or LAGE-1 expression in their tumor specimens. Due to the limited sample sizes, no statistical analysis was performed to assess the correlation between the presence of Ab and the expression of the specific TAA in this study. Nevertheless, as evident in the results summarized in the table, the epitopes of the present invention may be used to assay NY-ESO-1 expression in tumors.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

---

What is claimed is:

1. An isolated peptide consisting of SEQ ID NO:16.
2. A composition comprising the isolated peptide of claim 1.
3. A substrate which comprises the isolated peptide of claim 1 immobilized thereon.
4. A kit comprising the isolated peptide of claim 1 packaged together with at least one reagent.
5. An isolated complex comprising the isolated peptide of claim 1 and an antibody which selectively binds the peptide.
6. A method for assaying, enriching, isolating or purifying at least one antibody against a tumor associated antigen, or a B cell producing the antibody, which comprises contacting the antibody with the isolated peptide of claim 1.
7. A method which comprises contacting the isolated peptide of claim 1 with a sample and detecting whether an antibody in the sample selectively binds the peptide.
8. A method for detecting, diagnosing, or monitoring lung cancer in a subject which comprises contacting the isolated peptide of claim 1 with a sample obtained from the subject and detecting whether an antibody in the sample selectively binds the peptide.
9. The method of claim 8, wherein a plurality of samples otained from the subject are tested.
10. The method of claim 9, wherein the plurality of samples are obtained before, during or after treating the lung cancer.
11. The method of claim 10, wherein, the regression, recurrence or progression of the lung cancer is determined by observing any change or difference in the antibody selectively binding the peptide from the plurality of samples.

* * * * *

UNITED STATES PATENT AND TRADEMARK OFFICE
CERTIFICATE OF CORRECTION

PATENT NO. : 7,943,729 B2  Page 1 of 1
APPLICATION NO. : 12/182652
DATED : May 17, 2011
INVENTOR(S) : Gang Zeng It is certified that error appears in the above-identified patent and that said Letters Patent is hereby corrected as shown below:

In the Specification

In Column 1, lines 19-22:
Please change "This invention was made with Government support of Grant No. 1 P50 CA92131 and 1 P50 CA90388, awarded by the National Cancer Institute. The Government has certain rights in this invention." to --This invention was made with Government support under Grant Nos. CA090388 and CA092131 awarded by the National Institutes of Health. The Government has certain rights in this invention.-- ;

In Column 1, lines 23-26:
Please cancel the text beginning with "This research is" to and ending with "career development (1 P50 CA90388)."

Signed and Sealed this
Tenth Day of September, 2013

Teresa Stanek Rea
*Acting Director of the United States Patent and Trademark Office*